(12) United States Patent
Opshaug et al.

(10) Patent No.: US 11,570,789 B2
(45) Date of Patent: Jan. 31, 2023

(54) MULTI-USER-EQUIPMENT POSITIONING SIGNALING

(71) Applicant: QUALCOMM Incorporated, San Diego, CA (US)

(72) Inventors: Guttorm Ringstad Opshaug, Redwood City, CA (US); Alexandros Manolakos, Escondido, CA (US); Stephen William Edge, Escondido, CA (US); Sven Fischer, Nuremberg (DE)

(73) Assignee: QUALCOMM Incorporated, San Diego, CA (US)

( * ) Notice: Subject to any disclaimer, the term of this patent is extended or adjusted under 35 U.S.C. 154(b) by 0 days.

(21) Appl. No.: 17/089,618

(22) Filed: Nov. 4, 2020

(65) Prior Publication Data

US 2021/0136787 A1    May 6, 2021

Related U.S. Application Data

(60) Provisional application No. 62/931,240, filed on Nov. 6, 2019.

(51) Int. Cl.
*H04W 72/12* (2009.01)
*H04W 64/00* (2009.01)
*A61F 5/00* (2006.01)

(52) U.S. Cl.
CPC .......... *H04W 72/121* (2013.01); *A61F 5/005* (2013.01); *A61F 5/0086* (2013.01); *H04W 64/00* (2013.01);
(Continued)

(58) Field of Classification Search
CPC .......... H04W 72/121; H04W 72/1268; H04W 72/1289
See application file for complete search history.

(56) References Cited

U.S. PATENT DOCUMENTS 9,826,350 B1 * 11/2017 Wang ............... G01S 5/0226
2016/0128067 A1 * 5/2016 Seibert ............... G01S 1/20
370/329
(Continued)

OTHER PUBLICATIONS

Fraunhofer Iis: et al., "Aspects of UL-Based NR Positioning Techniques", 3GPP Draft, R1-1981183, NR Positioning UL, 3rd Generation Partnership Project (3GPP), Mobile Competence Centre, 650, Route Des Lucioles, F-06921 Sophia-Antipolis Cedex, France, vol. RAN WG1, No. Taipei, Taiwan, Jan. 21, 2019-Jan. 25, 2019, Jan. 20, 2019 (Jan. 20, 2019), XP051594026, Retrieved from the Internet: URL: http://www.3gpp.org/ftp/Meetings%5F3GPP%5FSYNC/RAN1/Docs/R1%2D1901183%2Ezip. [retrieved on Jan. 20, 2019] sections 1-5.
(Continued)

*Primary Examiner* — Michael T Vu
(74) *Attorney, Agent, or Firm* — Thien T. Nguyen

(57) ABSTRACT

A method of coordinating positioning signaling includes: identifying a first user equipment (UE) served by a base station and a second UE served by the base station, the base station being configured to send a base station positioning signal wirelessly at a plurality of base-station-transmission times; allocating first times to the first UE, for sending first UE positioning signals, and second times to the second UE, for sending second UE positioning signals, at least one of the first times being different from at least one of the second times; sending a first communication to cause the first UE to send at least a respective one of the first UE positioning signals at each of the first times; and sending a second communication to cause the second UE to send at least a respective one of the second UE positioning signals at each of the second times.

44 Claims, 7 Drawing Sheets

(52) U.S. Cl.
CPC ... *H04W 72/1268* (2013.01); *H04W 72/1289* (2013.01)

(56) References Cited

U.S. PATENT DOCUMENTS

2018/0184452 A1* 6/2018 Bitra ................ H04W 72/1215
2022/0265453 A1 8/2022 Opshaug

OTHER PUBLICATIONS

Nokia et al., "Potental Positioning Techniques—UL Based Solutions", 3GPP Draft, R1-1901848, UL NR Positioning, 3rd Generation Partnership Project (3GPP), Mobile Competence Centre, 650, Route Des Lucioles, F-06921 Sophia-Antipolis Cedex, France, vol. RAN WG1, No. Athens, Greece, Feb. 25, 2019-Mar. 1, 2019, Feb. 15, 2019 (Feb. 15, 2019), XP051599541, 6 Pages, Retrieved from the Internet: URL: http://www.3gpp.org/ftp/tsg%5Fran/WG1%5FRL1/TSGR1%5F96/Docs/R1%2D1901848%2Ezip. [retrieved on Feb. 15, 2019] sections 1-3.
Fraunhofer Iis, et al., "UE Procedures for Transmitting UL PRS", 3GPP Draft, 3GPP TSG RAN WG1 Meeting #97, R1-1907089, ULPRS Procedures, 3rd Generation Partnership Project (3GPP), Mobile Competence Centre, 650, Route Des Lucioles, F-06921 Sophia-Antipolis Cedex, France, vol. RAN WG1, No. Reno, US, May 13, 2019-May 17, 2019, May 13, 2019 (May 13, 2019), XP051728535, 10 Pages, Retrieved from the Internet: URL: http://www.3gpp.org/ftp/Meetings%5F3GPP%5FSYNC/RAN1/Docs/R1%2D1907089%2Ezip. [retrieved on May 13, 2019] sections 1-6.
International Search Report and Written Opinion—PCT/US2020/059011—ISA/EPO—dated Jan. 27, 2021.
Nokia, et al., "Potential Positioning Techniques—UL Based Solutions", 3GPP Draft, R1-1901848, UL NR Positioning, 3rd Generation Partnership Project (3GPP), Mobile Competence Centre, 650, Route Des Lucioles, F-06921 Sophia-Antipolis Cedex, France, vol. RAN WG1, No. Athens, Greece, Feb. 25, 2019-Mar. 1, 2019, Feb. 15, 2019 (Feb. 15, 2019), XP051599541, 6 Pages, Retrieved from the Internet: URL: http://www.3gpp.org/ftp/tsg%5Fran/WG1%5FRL1/TSGR1%5F96/Docs/R1%2D1901848%2Ezip. [retrieved on Feb. 15, 2019] sections 1-3.
Qualcomm Incorporated: "On UE Rx-Tx Time Difference Measurements for NR Positioning", 3GPP TSG-RAN WG4 Meeting #94-e, R4-2000733, 3rd Generation Partnership Project, Mobile Competence Centre, 650, Route Des Lucioles, F-06921 Sophia-Antipolis Cedex, France, vol. RAN WG4, No. Online, Feb. 24, 2020-Mar. 6, 2020, Feb. 14, 2020, XP051850704, 15 pages.

* cited by examiner

MULTI-USER-EQUIPMENT POSITIONING SIGNALING

CROSS-REFERENCE TO RELATED APPLICATION

This application claims the benefit of U.S. Provisional Application No. 62/931,240, filed Nov. 6, 2019, entitled "MULTI-USER-EQUIPMENT POSITIONING SIGNALING," which is assigned to the assignee hereof, and the entire contents of which are hereby incorporated herein by reference for all purposes.

BACKGROUND

Wireless communication systems have developed through various generations, including a first-generation analog wireless phone service (1G), a second-generation (2G) digital wireless phone service (including interim 2.5G and 2.75G networks), a third-generation (3G) high speed data, Internet-capable wireless service and a fourth-generation (4G) service (e.g., Long Term Evolution (LTE) or WiMax), fifth-generation (5G) service, etc. There are presently many different types of wireless communication systems in use, including Cellular and Personal Communications Service (PCS) systems. Examples of known cellular systems include the cellular Analog Advanced Mobile Phone System (AMPS), and digital cellular systems based on Code Division Multiple Access (CDMA), Frequency Division Multiple Access (FDMA), Orthogonal Frequency Division Multiple Access (OFDMA), Time Division Multiple Access (TDMA), the Global System for Mobile access (GSM) variation of TDMA, etc.

A fifth generation (5G) mobile standard calls for higher data transfer speeds, greater numbers of connections, and better coverage, among other improvements. The 5G standard, according to the Next Generation Mobile Networks Alliance, is designed to provide data rates of several tens of megabits per second to each of tens of thousands of users, with 1 gigabit per second to tens of workers on an office floor. Several hundreds of thousands of simultaneous connections should be supported in order to support large sensor deployments. Consequently, the spectral efficiency of 5G mobile communications should be significantly enhanced compared to the current 4G standard. Furthermore, signaling efficiencies should be enhanced and latency should be substantially reduced compared to current standards.

Obtaining the locations of mobile devices that are accessing a wireless network may be useful for many applications including, for example, emergency calls, personal navigation, asset tracking, locating a friend or family member, etc. Existing positioning methods include methods based on measuring radio signals transmitted from a variety of devices or entities including satellite vehicles (SVs) and terrestrial radio sources in a wireless network such as base stations and access points. It is expected that standardization for the 5G wireless networks will include support for various positioning methods, which may utilize reference signals transmitted by base stations in a manner similar to which LTE wireless networks currently utilize Positioning Reference Signals (PRS) and/or Cell-specific Reference Signals (CRS) for position determination.

SUMMARY

An example method of coordinating positioning signaling includes: identifying a first user equipment (UE) served by a base station and a second UE served by the base station, the base station being configured to send a base station positioning signal wirelessly at a plurality of base-station-transmission times; allocating first times to the first UE, for sending first UE positioning signals, and second times to the second UE, for sending second UE positioning signals, at least one of the first times being different from at least one of the second times; sending a first communication to cause the first UE to send at least a respective one of the first UE positioning signals at each of the first times; and sending a second communication to cause the second UE to send at least a respective one of the second UE positioning signals at each of the second times.

Implementations of such a method may include one or more of the following features. The first times occur less often than the plurality of base-station-transmission times. The first times and the second times are allocated to be proximate in time to respective ones of the plurality of base-station-transmission times. The method includes controlling the base station to listen for the first UE positioning signals only during first-signal-measurement times. The first-signal-measurement times include the first times offset for travel time between the first UE and the base station.

Also or alternatively, implementations of such a method may include one or more of the following features. Each respective one of the first times is before a respective one of the plurality of base-station-transmission times to which the respective one of the first times is closest in time. The first times and the second times include a plurality of pairs of times, and each of the plurality of pairs of times includes: a respective one of the first times that is closest in time, of the first times, to a respective one of the plurality of base-station-transmission times; and a respective one of the second times that is closest in time, of the second times, to the respective one of the plurality of base-station-transmission times, and the respective one of the first times is different than the respective one of the second times. The method includes sending a third communication to change the first times to third times, at least one of the third times being different from the first times. The method includes causing the base station to change the plurality of base-station-transmission times in response to a trigger condition. The trigger condition is a threshold quantity of UEs being exceeded. The threshold quantity of UEs is a threshold quantity of UEs per epoch.

Also or alternatively, implementations of such a method may include one or more of the following features. All of the first times are different from all of the second times. The first times alternate in time with the second times. The first times and the second times are respective time portions of a set of sequence frames, and the set of sequence frames repeats.

An example system for coordinating positioning signaling includes: a transceiver; and a processor communicatively coupled to the transceiver and configured to: identify a first user equipment (UE) served by a base station and a second UE served by the base station, the base station being configured to send a base station positioning signal wirelessly at a plurality of base-station-transmission times; allocate first times to the first UE, for sending first UE positioning signals, and second times to the second UE, for sending second UE positioning signals, at least one of the first times being different from at least one of the second times; send a first communication, via the transceiver, to cause the first UE to send at least a respective one of the first UE positioning signals at each of the first times; and send a second communication, via the transceiver, to cause the second UE to send at least a respective one of the second UE positioning signals at each of the second times.

Implementations of such a system may include one or more of the following features. The processor is configured to allocate the first times such that the first times are less frequent than the plurality of base-station-transmission times. The processor is configured to allocate the first times and the second times to be proximate in time to respective ones of the plurality of base-station-transmission times. The processor is configured to control the base station to listen for the first UE positioning signals only during first-signal-measurement times. The first-signal-measurement times include the first times offset for travel time between the first UE and the base station.

Also or alternatively, implementations of such a system may include one or more of the following features. The processor is configured to allocate the first times and the second times such that: the first times and the second times include a plurality of pairs of times; each of the plurality of pairs of times includes: a respective one of the first times that is closest in time, of the first times, to a respective one of the plurality of base-station-transmission times; and a respective one of the second times that is closest in time, of the second times, to the respective one of the plurality of base-station-transmission times; and the respective one of the first times is different than the respective one of the second times. The processor is configured to send a third communication to change the first times to third times, at least one of the third times being different from the first times. The processor is configured to cause the base station to change the plurality of base-station-transmission times in response to a trigger condition. The trigger condition is a threshold quantity of UEs being exceeded. The threshold quantity of UEs is a threshold quantity of UEs per epoch.

Another example system for coordinating positioning signaling includes: means for identifying a first user equipment (UE) served by a base station and a second UE served by the base station, the base station being configured to send a base station positioning signal wirelessly at a plurality of base-station-transmission times; means for allocating first times to the first UE, for sending first UE positioning signals, and second times to the second UE, for sending second UE positioning signals, at least one of the first times being different from at least one of the second times; means for sending a first communication to cause the first UE to send at least a respective one of the first UE positioning signals at each of the first times; and means for sending a second communication to cause the second UE to send at least a respective one of the second UE positioning signals at each of the second times.

Implementations of such a system may include one or more of the following features. The means for allocating are for allocating the first times such that the first times occur less often than the plurality of base-station-transmission times. The means for allocating are for allocating the first times and the second times to be proximate in time to respective ones of the plurality of base-station-transmission times. The system includes means for controlling the base station to listen for the first UE positioning signals only during first-signal-measurement times. The first-signal-measurement times include the first times offset for travel time between the first UE and the base station.

Also or alternatively, implementations of such a system may include one or more of the following features. The means for allocating are for allocating the first times and the second times such that: the first times and the second times include a plurality of pairs of times; each of the plurality of pairs of times includes: a respective one of the first times that is closest in time, of the first times, to a respective one of the plurality of base-station-transmission times; and a respective one of the second times that is closest in time, of the second times, to the respective one of the plurality of base-station-transmission times; and the respective one of the first times is different than the respective one of the second times. The system includes means for sending a third communication to change the first times to third times, at least one of the third times being different from the first times. The system includes means for causing the base station to change the plurality of base-station-transmission times in response to a trigger condition. The trigger condition is a threshold quantity of UEs being exceeded. The threshold quantity of UEs is a threshold quantity of UEs per epoch.

An example non-transitory, processor-readable storage medium includes processor-readable instructions configured to cause a processor to: identify a first user equipment (UE) served by a base station and a second UE served by the base station, the base station being configured to send a base station positioning signal wirelessly at a plurality of base-station-transmission times; allocate first times to the first UE, for sending first UE positioning signals, and second times to the second UE, for sending second UE positioning signals, at least one of the first times being different from at least one of the second times; send a first communication to cause the first UE to send at least a respective one of the first UE positioning signals at each of the first times; and send a second communication to cause the second UE to send at least a respective one of the second UE positioning signals at each of the second times.

Implementations of such a storage medium may include one or more of the following features. The instructions configured to allocate the first times are configured to allocate the first times such that the first times occur less often than the plurality of base-station-transmission times. The instructions configured to allocate the first times and the second times are configured to allocate the first times and the second times to be proximate in time to respective ones of the plurality of base-station-transmission times. The storage medium includes instructions configured to cause the base station to listen for the first UE positioning signals only during first-signal-measurement times. The first-signal-measurement times include the first times offset for travel time between the first UE and the base station.

Also or alternatively, implementations of such a storage medium may include one or more of the following features. The first times and the second times include a plurality of pairs of times, each of the plurality of pairs of times includes: a respective one of the first times that is closest in time, of the first times, to a respective one of the plurality of base-station-transmission times; and a respective one of the second times that is closest in time, of the second times, to the respective one of the plurality of base-station-transmission times, and the respective one of the first times is different than the respective one of the second times. The storage medium includes instructions configured to cause the processor to send a third communication to change the first times to third times, at least one of the third times being different from the first times. The storage medium includes instructions configured to cause the processor to cause the base station to change the plurality of base-station-transmission times in response to a trigger condition. The trigger condition is a threshold quantity of UEs being exceeded. The threshold quantity of UEs is a threshold quantity of UEs per epoch.

Another example method of coordinating positioning signaling includes: sending, from a user equipment (UE), a request wirelessly for positioning service; receiving, at the UE, an indication of UE positioning signal times for sending UE positioning signals; and sending, from the UE, the UE positioning signals at the UE positioning signal times.

Implementations of such a method may include one or more of the following features. The indication of UE positioning signal times includes a schedule of times within a set of sequence frames. The indication of UE positioning signal times includes a schedule of base station positioning signals and an indication of a subset of base-station-transmission times corresponding to a subset of the base station positioning signals.

An example user equipment (UE) includes: a transceiver; and a processor communicatively coupled to the transceiver and configured to: send, via the transceiver, a wireless request for positioning service; receive, via the transceiver, an indication of UE positioning signal times for sending UE positioning signals; and send, via the transceiver, the UE positioning signals wirelessly at the UE positioning signal times.

Implementations of such a UE may include one or more of the following features. The indication of UE positioning signal times includes a schedule of times within a set of sequence frames. The indication of UE positioning signal times includes an indication of a subset of base-station-transmission times corresponding to a subset of the base station positioning signals.

Another example UE includes: means for sending a request wirelessly for positioning service; means for receiving an indication of UE positioning signal times for sending UE positioning signals; and means for sending the UE positioning signals at the UE positioning signal times.

Implementations of such a UE may include one or more of the following features. The indication of UE positioning signal times includes a schedule of times within a set of sequence frames. The indication of UE positioning signal times includes a schedule of base station positioning signals and an indication of a subset of base-station-transmission times corresponding to a subset of the base station positioning signals.

Another example non-transitory, processor-readable storage medium includes processor-readable instructions configured to cause a processor to: send, from a user equipment (UE) via a transceiver of the UE, a request wirelessly for positioning service, receive, at the UE, an indication of UE positioning signal times for sending UE positioning signals; and send, from the UE via the transceiver, the UE positioning signals at the UE positioning signal times.

Implementations of such a storage medium may include one or more of the following features. The indication of UE positioning signal times includes a schedule of times within a set of sequence frames. The indication of UE positioning signal times includes a schedule of base station positioning signals and an indication of a subset of base-station-transmission times corresponding to a subset of the base station positioning signals.

DETAILED DESCRIPTION

Techniques are discussed herein for coordinating positioning signaling. For example, a server (or other device such as a Transmission/Reception Point (TRP)) may allocate times for UEs to send uplink positioning signals. The server may coordinate the allocated times to distribute times at which uplink positioning signals are sent by UEs and/or measured and processed by a TRP. The server may allocate the uplink signaling times so that different UEs send uplink positioning signals at different times. The server may instruct TRPs to measure signals corresponding to the UEs only during windows of tune that correspond to the uplink signaling times for the respective UEs (e.g., that include the uplink signaling times offset by travel times from the UEs to the TRP). The server may determine the allocations of times in response to one or more trigger conditions such as the number of UEs expected to send uplink positioning signals (e.g., using and requesting location service). The server may dynamically change the allocations of times as conditions change as the number of UEs expected to send uplink positioning signals changes). Other configurations, however, may be used.

Items and/or techniques described herein may provide one or more of the following capabilities, as well as other capabilities not mentioned. Radio frequency signal congestion may be reduced in a wireless communication system. Signal processing congestion may be reduced in a wireless communication system. A user equipment capacity of a wireless communication system may be increased, e.g., for user equipment receiving and/or requesting location service. Other capabilities may be provided and not every implementation according to the disclosure must provide any, let alone of the capabilities discussed.

Figure 1:
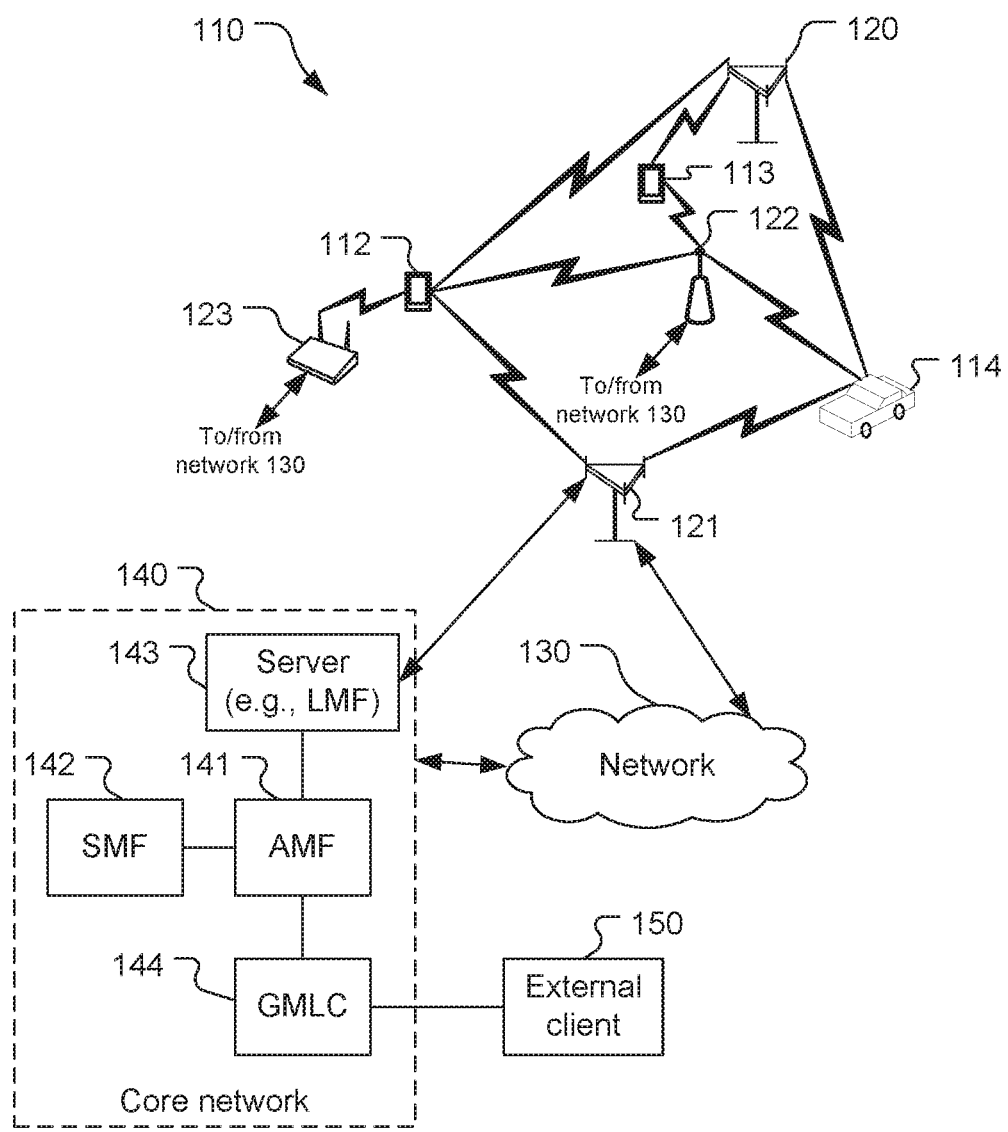
FIG. 1 is a simplified diagram of an example wireless communications system.

Referring to FIG. 1, an example wireless communications system 110 includes a user equipment (UE) 112, a UE 113, a UE 114, base transceiver stations (BTSs) 120, 121, 122, 123, a network 130, a core network 140, and an external client 150. The core network 140 (e.g., a 5G core network (5GC)) may include back-end devices including, among other things, an Access and Mobility Management Function (AMF) 141, a Session Management Function (SMF) 142, a server 143, and a Gateway Mobile Location Center (GMLC) 144. The AMF 141, the SMF 142, the server 143, and the GMLC 144 are communicatively coupled to each other. The server 143 may be, for example, a Location Management Function (LMF) that supports positioning of the UEs 112-114 (e.g., using techniques such as Assisted Global Navigation Satellite System (A-GNSS), OTDOA (Observed Time Difference of Arrival, Downlink (DL) OTDOA and/or Uplink (UL) OTDOA), Round Trip Time (RTT), Multi-Cell RTT, RTK (Real Time Kinematic), PPP (Precise Point Positioning), DGNSS (Differential GNSS), E-CID (Enhanced Cell ID), AOA (Angle of Arrival), AoD (Angle of Departure), etc.).

An LMF may also be referred to as a Location Manager (LM), a Location Function (LF), a commercial LMF (CLMF), or a value-added LMF (VLMF). The server 143 (e.g., an LMF) and/or one or more other devices of the system 110 (e.g., one or more of the UEs 112-114) may be configured to determine locations of the UEs 112-114. The server 143 may communicate directly with the BTS 121 (e.g., a gNB) and/or one or more other BTSs, and may be integrated with the BTS 121 and/or one or more other BTSs. The SMF 142 may serve as an initial contact point of a Service Control Function (SCF) (not shown) to create, control, and delete media sessions. The server 143 (e.g., an LMF) may be co-located or integrated with a gNB or a TRP (Transmission/Reception Point), or may be disposed remotely from the gNB and/or the TRP and configured to communicate directly or indirectly with the gNB and/or the TRP.

The AMF 141 may serve as a control node that processes signaling between the UEs 112-114 and the core network 140, and provides QoS (Quality of Service) flow and session management. The AMF 141 may support mobility of the UEs 112-114 including cell change and handover and may participate in supporting signaling connection to the UEs 112-114.

The system 110 is capable of wireless communication in that components of the system 110 can communicate with one another (at least some times using wireless connections) directly or indirectly, e.g., via the BTSs 120-123 and/or the network 130 (and/or one or more other devices not shown, such as one or more other base transceiver stations). For indirect communications, the communications may be altered during transmission from one entity to another, e.g., to alter header information of data packets, to change format, etc. The UEs 112-114 shown are a smartphone, a tablet computer, and a vehicle-based device, but these are examples only as the UEs 112-114 are not required to be any of these configurations, and other configurations of UEs may be used. The UEs 112, 113 shown are mobile wireless communication devices (although they may communicate wirelessly and via wired connections) including mobile phones (including smartphones) and a tablet computer. The UE 114 shown is a vehicle-based mobile wireless communication device (although the UE 114 may communicate wirelessly and via wired connections). Other UEs may include wearable devices (e.g., smart watches, smart jewelry, smart glasses or headsets, etc.). Still other UEs may be used, whether currently existing or developed in the future. Further, other wireless devices (whether mobile or not) may be implemented within the system 110 and may communicate with each other and/or with the UEs 112-114, the BTSs 120-123, the network 130, the core network 140, and/or the external client 150. For example, such other devices may include internet of thing (IoT) devices, medical devices, home entertainment and/or automation devices, etc. The core network 140 may communicate with the external client 150 (e.g., a computer system), e.g., to allow the external client 150 to request and/or receive location information regarding the UEs 112-114 (e.g., via the GMLC 144).

The UEs 112-114 or other devices may be configured to communicate in various networks and/or for various purposes and/or using various technologies (e.g., 5G, Wi-Fi communication, multiple frequencies of Wi-Fi communication, satellite positioning, one or more types of communications (e.g., GSM (Global System for Mobiles), CDMA (Code Division Multiple Access), LTE (Long-Term Evolution), V2X (e.g., V2P (Vehicle-to-Pedestrian), V2I (Vehicle-to-Infrastructure), V2V (Vehicle-to-Vehicle), etc.), IEEE 802.11p, etc.). V2X communications may be cellular (Cellular-V2X (C-V2X)) and/or WiFi (e.g., DSRC (Dedicated Short-Range Connection)). The system 110 may support operation on multiple carriers (waveform signals of different frequencies). Multi-carrier transmitters can transmit modulated signals simultaneously on the multiple carriers. Each modulated signal may be a Code Division Multiple Access (CDMA) signal, a Time Division Multiple Access (TDMA) signal, an Orthogonal Frequency Division Multiple Access (OFDMA) signal, a Single-Carrier Frequency Division Multiple Access (SC-FDMA) signal, etc. Each modulated signal may be sent on a different carrier and may carry pilot, overhead information, data, etc.

The BTSs 120-123 may wirelessly communicate with the UEs 112-114 in the system 110 via one or more antennas. A BTS may also be referred to as a base station, an access point, a gNode B (gNB), an access node (AN), a Node B, an evolved Node B (eNB), etc. For example, each of the BTSs 120, 121 may be a gNB or a transmission point gNB, the BTS 122 may be a macro cell (e.g., a high-power cellular base station) and/or a small cell (e.g., a low-power cellular base station), and the BTS 123 may be an access point (e.g., a short-range base station configured to communicate with short-range technology such as WiFi, WiFi-Direct Bluetooth®, Bluetooth®-low energy (BLE), Zigbee, etc. One or more of the BTSs 120-123 may be configured to communicate with the UEs 112-114 via multiple carriers. Each of the BTSs 120, 121 may provide communication coverage for a respective geographic region, e.g. a cell. Each cell may be partitioned into multiple sectors as a function of the base station antennas.

The BTSs 120-123 each comprise one or more Transmission/Reception Points (TRPs). For example, each sector within a cell of a BTS may comprise a TRP, although multiple TRPs may share one or more components (e.g., share a processor but have separate antennas). The system 110 may include only macro TRPs or the system 110 may have TRPs of different types, e.g., macro, pico, and/or femto TRPs, etc. A macro TRP may cover a relatively large geographic area (e.g., several kilometers in radius) and may allow unrestricted access by terminals with service subscription. A pico TRP may cover a relatively small geographic area (e.g., a pico cell) and may allow unrestricted access by terminals with service subscription. A femto or home TRP may cover a relatively small geographic area (e.g., a femto cell) and may allow restricted access by terminals having association with the femto cell (e.g., terminals for users in a home).

The UEs 112-114 may be referred to as terminals, access terminals (ATs), mobile stations, mobile devices, subscriber units, etc. The UEs 112-114 may include various devices as listed above and/or other devices. The UEs 112-114 may be configured to connect indirectly to one or more communication networks via one or more device-to-device (D2D) peer-to-peer (P2P) links. The D2D P2P links may be supported with any appropriate D2D radio access technology (RAT), such as LTE Direct (LTE-D), WiFi Direct (WiFi-D), Bluetooth®, and so on. One or more of a group of the UEs 112-114 utilizing D2D communications may be within a geographic coverage area of a TRP such as one or more of the BTSs 120-123. Other UEs in such a group may be outside such geographic coverage areas, or be otherwise unable to receive transmissions from a base station. Groups of the UEs 112-114 communicating via D2D communications may utilize a one-to-many (1:M) system in which each UE may transmit to other UEs in the group. A TRP of the BTSs 120-123 may facilitate scheduling of resources for D2D communications. In other cases, D2D communications may be carried out between UEs without the involvement of a TRP.

Figure 2:
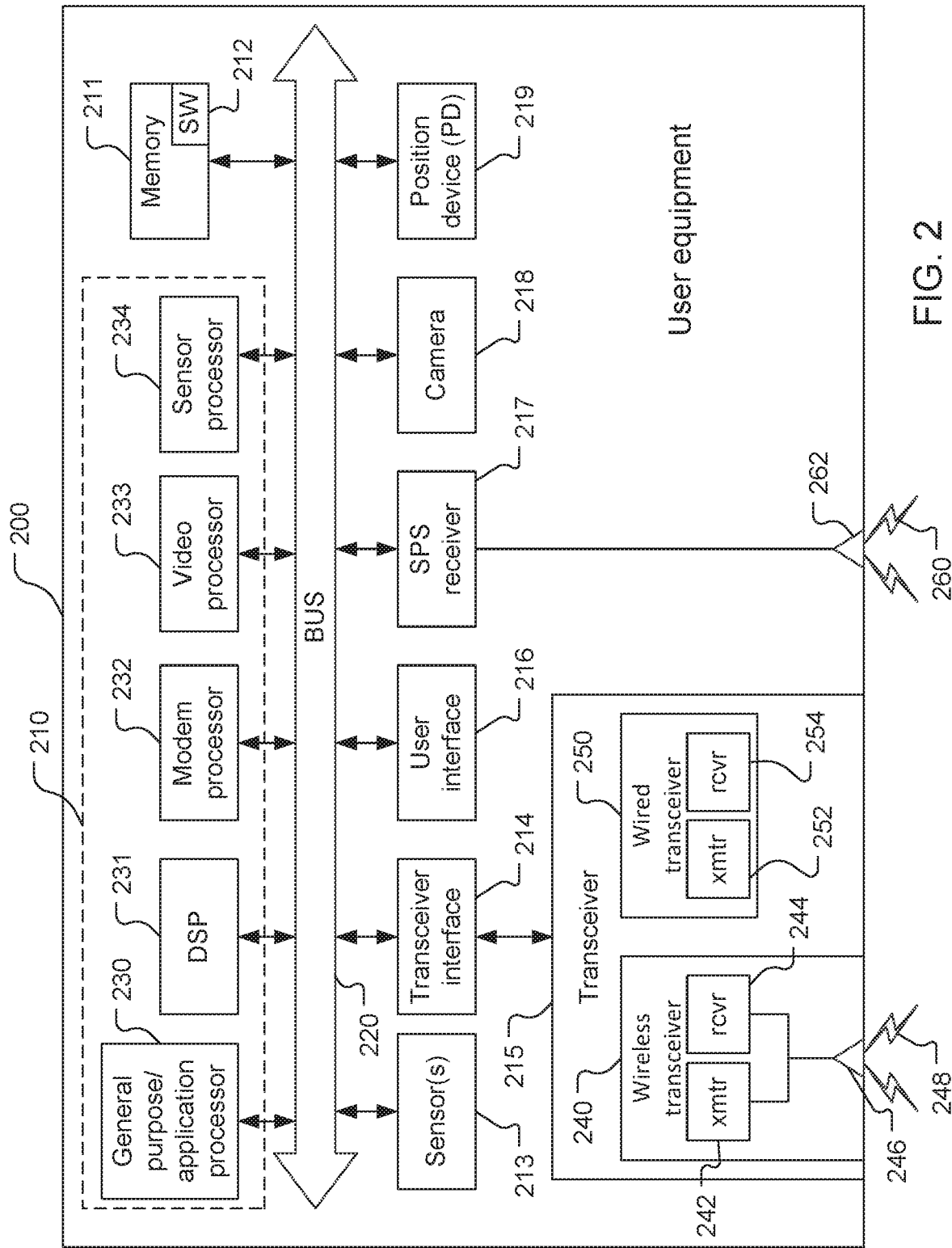
FIG. 2 is a block diagram of components of an example user equipment shown in FIG. 1.

Referring also to FIG. 2, a UE 200 is an example of one of the UEs 112-114 and comprises a computing platform including a processor 210, memory 211 including software (SW) 212, one or more sensors 213, a transceiver interface 214 for a transceiver 215, a user interface 216, a Satellite Positioning System (SPS) receiver 217, a camera 218, and a position device 219. The processor 210, the memory 211, the sensor(s) 213, the transceiver interface 214, the user interface 216, the SPS receiver 217, the camera 218, and the PD 219 may be communicatively coupled to each other by a bus 220 (which may be configured, e.g., for optical and/or electrical communication). One or more of the shown apparatus (e.g., the camera 218, the PD 219, and/or one or more of the sensor(s) 213, etc.) may be omitted from the UE 200. The processor 210 may include one or more intelligent hardware devices, e.g., a central processing unit (CPU), a microcontroller, an application specific integrated circuit (ASIC), etc. The processor 210 may comprise multiple processors including a general-purpose/application processor 230, a Digital Signal Processor (DSP) 231, a modem processor 232, a video processor 233, and/or a sensor processor 234. One or more of the processors 230-234 may comprise multiple devices (e.g., multiple processors). For example, the sensor processor 234 may comprise, e.g., processors for radar, ultrasound, and/or lidar, etc. The modem processor 232 may support dual SIM/dual connectivity (or even more SIMs). For example, a SIM (Subscriber Identity Module or Subscriber Identification Module) may be used by an Original Equipment Manufacturer (OEM), and another SIM may be used by an end user of the UE 200 for connectivity. The memory 211 is a non-transitory storage medium that may include random access memory (RAM), flash memory, disc memory, and/or read-only memory (ROM), etc. The memory 211 stores the software 212 which may be processor-readable, processor-executable software code containing instructions that are configured to, when executed, cause the processor 210 to perform various functions described herein. Alternatively, the software 212 may not be directly executable by the processor 210 but may be configured to cause the processor 210, e.g., when compiled and executed, to perform the functions. The description may refer only to the processor 210 performing a function, but this includes other implementations such as where the processor 210 executes software and/or firmware. The description may refer to the processor 210 performing a function as shorthand for one or more of the processors 230-234 performing the function. The description may refer to the UE 200 performing a function as shorthand for one or more appropriate components of the UE 200 performing the function. The processor 210 may include a memory with stored instructions in addition to and/or instead of the memory 211. Functionality of the processor 210 is discussed more fully below.

The configuration of the UE 200 shown in FIG. 2 is an example and not limiting of the invention, including the claims, and other configurations may be used. For example, an example configuration of the UE includes one or more of the processors 230-234 of the processor 210, the memory 211, and the wireless transceiver 240. Other example configurations include one or more of the processors 230-234 of the processor 210, the memory 211, the wireless transceiver 240, and one or more of the sensor(s) 213, the user interface 216, the SPS receiver 217, the camera 218, the PD 219, and/or the wired transceiver 250.

The UE 200 may comprise the modem processor 232 that may be capable of performing baseband processing of signals received and down-converted by the transceiver 215 and/or the SPS receiver 217. The modem processor 232 may perform baseband processing of signals to be upconverted for transmission by the transceiver 215. Also or alternatively, baseband processing may be performed by the processor 230 and/or the DSP 231. Other configurations, however, may be used to perform baseband processing.

The UE 200 may include the sensor(s) 213 that may include, for example, one or more of various types of sensors such as one or more inertial sensors, one or more magnetometers, one or more environmental sensors, one or more optical sensors, one or more weight sensors, and/or one or more radio frequency (RF) sensors, etc. An inertial measurement unit (IMU) may comprise, for example, one or more accelerometers (e.g., collectively responding to acceleration of the UE 200 in three dimensions) and/or one or more gyroscopes. The sensor(s) 213 may include one or more magnetometers to determine orientation (e.g., relative to magnetic north and/or true north) that may be used for any of a variety of purposes, e.g., to support one or more compass applications. The environment sensor(s) may comprise, for example, one or more temperature sensors, one or more barometric pressure sensors, one or more ambient light sensors, one or more camera imagers, and/or one or more microphones, etc. The sensor(s) 213 may generate analog and/or digital signals indications of which may be stored in the memory 211 and processed by the DSP 231 and/or the processor 230 in support of one or more applications such as, for example, applications directed to positioning and/or navigation operations.

The sensor(s) 100 may be used in relative location measurements, relative location determination, motion determination, etc. Information detected by the sensor(s) 100 may be used for motion detection, relative displacement, dead reckoning, sensor-based location determination, and/or sensor-assisted location determination. The sensor(s) 100 may be useful to determine whether the UE 200 is fixed (stationary) or mobile and/or whether to report certain useful information to the server 143 regarding the mobility of the UE 200. For example, based on the information obtained/measured by the sensor(s), the UE 200 may notify/report to the server 143 that the UE 200 has detected movements or that the UE 200 has moved, and report the relative displacement/distance (e.g., via dead reckoning, or sensor-based location determination, or sensor-assisted location determination enabled by the sensor(s) 100). In another example, for relative positioning information, the sensors/IMU can be used to determine the angle and/or orientation of the other device with respect to the UE 200, etc.

The IMU may be configured to provide measurements about a direction of motion and/or a speed of motion of the UE 200, which may be used in relative location determination. For example, one or more accelerometers and/or one or more gyroscopes of the IMU may detect, respectively, a linear acceleration and a speed of rotation of the UE 200. The linear acceleration and speed of rotation measurements of the UE 200 may be integrated over time to determine an instantaneous direction of motion as well as a displacement of the UE 200. The instantaneous direction of motion and the displacement may be integrated to track a location of the UE 200. For example, a reference location of the UE 200 may be determined, e.g., using the SPS receiver 217 (and/or by some other means) for a moment in time and measurements from the accelerometer(s) and gyroscope(s) taken after this moment in time may be used in dead reckoning to determine present location of the UE 200 based on movement (direction and distance) of the UE 200 relative to the reference location.

The magnetometer(s) may determine magnetic field strengths in different directions which may be used to determine orientation of the UE 200. For example, the orientation may be used to provide a digital compass for the UE 200. The magnetometer may be a two-dimensional magnetometer configured to detect and provide indications of magnetic field strength in two orthogonal dimensions. Alternatively, the magnetometer may be a three-dimensional magnetometer configured to detect and provide indications of magnetic field strength in three orthogonal dimensions. The magnetometer may provide means for sensing a magnetic field and providing indications of the magnetic field, e.g., to the processor 210.

The transceiver 215 may include a wireless transceiver 240 and a wired transceiver 250 configured to communicate with other devices through wireless connections and wired connections, respectively. For example, the wireless transceiver 240 may include a transmitter 242 and receiver 244 coupled to one or more antennas 246 for transmitting (e.g., on one or more uplink channels) and/or receiving (e.g., on one or more downlink channels) wireless signals 248 and transducing signals from the wireless signals 248 to wired (e.g., electrical and/or optical) signals and from wired (e.g., electrical and/or optical) signals to the wireless signals 248. Thus, the transmitter 242 may include multiple transmitters that may be discrete components or combined/integrated components, and/or the receiver 244 may include multiple receivers that may be discrete components or combined/integrated components. The wireless transceiver 240 may be configured to communicate signals (e.g., with TRPs and/or one or more other devices) according to a variety of radio access technologies (RATS) such as 5G New Radio (NR), GSM (Global System for Mobiles), UMTS (Universal Mobile Telecommunications System), AMPS (Advanced Mobile Phone System), CDMA (Code Division Multiple Access), WCDMA (Wideband CDMA), LTE (Long-Term Evolution), LTE Direct (LTE-D), 3GPP LTE-V2X (PC5), IEEE 802.11 (including IEEE 802.11p), WiFi, WiFi Direct (WiFi-D), Bluetooth®, Zigbee etc. New Radio may use mm-wave frequencies and/or sub-6 GHz frequencies. The wired transceiver 250 may include a transmitter 252 and a receiver 254 configured for wired communication, e.g., with the network 130 to send communications to, and receive communications from, the UE 200, for example. The transmitter 252 may include multiple transmitters that may be discrete components or combined/integrated components, and/or the receiver 254 may include multiple receivers that may be discrete components or combined/integrated components. The wired transceiver 250 may be configured, e.g., for optical communication and/or electrical communication. The transceiver 215 may be communicatively coupled to the transceiver interface 214, e.g., by optical and/or electrical connection. The transceiver interface 214 may be at least partially integrated with the transceiver 215.

The user interface 216 may comprise one or more of several devices such as, for example, a speaker, microphone, display device, vibration device, keyboard, touch screen, etc. The user interface 216 may include more than one of any of these devices. The user interface 216 may be configured to enable a user to interact with one or more applications hosted by the UE 200. For example, the user interface 216 may store indications of analog and/or digital signals in the memory 211 to be processed by DSP 231 and/or the general-purpose processor 230 in response to action from a user. Similarly, applications hosted on the UE 200 may store indications of analog and/or digital signals in the memory 211 to present an output signal to a user. The user interface 216 may include an audio input/output (I/O) device comprising, for example, a speaker, a microphone, digital-to-analog circuitry, analog-to-digital circuitry, an amplifier and/or gain control circuitry (including more than one of any of these devices). Other configurations of an audio I/O device may be used. Also or alternatively, the user interface 216 may comprise one or more touch sensors responsive to touching and/or pressure, e.g., on a keyboard and/or touch screen of the user interface 216.

The SPS receiver 217 (e.g., a Global Positioning System (GPS) receiver) may be capable of receiving and acquiring SPS signals 260 via an SPS antenna 262. The antenna 262 is configured to transduce the wireless signals 260 to wired signals, e.g., electrical or optical signals, and may be integrated with the antenna 246. The SPS receiver 217 may be configured to process, in whole or in part, the acquired SPS signals 260 for estimating a location of the UE 200. For example, the SPS receiver 217 may be configured to determine location of the UE 200 by trilateration using the SPS signals 260. The general-purpose processor 230, the memory 211, the DSP 231 and/or one or more specialized processors (not shown) may be utilized to process acquired SPS signals, in whole or in part, and/or to calculate an estimated location of the UE 200, in conjunction with the SPS receiver 217. The memory 211 may store indications (e.g., measurements) of the SPS signals 260 and/or other signals (e.g., signals acquired from the wireless transceiver 240) for use in performing positioning operations. The general-purpose processor 230, the DSP 231, and/or one or more specialized processors, and/or the memory 211 may provide or support a location engine for use in processing measurements to estimate a location of the UE 200.

The UE 200 may include the camera 218 for capturing still or moving imagery. The camera 218 may comprise, for example, an imaging sensor (e.g., a charge coupled device or a CMOS imager), a lens, analog-to-digital circuitry, frame buffers, etc. Additional processing, conditioning, encoding, and/or compression of signals representing captured images may be performed by the general-purpose processor 230 and/or the DSP 231. Also or alternatively, the video processor 233 may perform conditioning, encoding, compression, and/or manipulation of signals representing captured images. The video processor 233 may decode/decompress stored image data for presentation on a display device (not shown), e.g., of the user interface 216.

The PD 219 may be configured to determine a position of the UE 200, motion of the UE 200, and/or relative position of the UE 200, and/or time. For example, the PD 219 may communicate with, and/or include some or all of, the SPS receiver 217. The PD 219 may work in conjunction with the processor 210 and the memory 211 as appropriate to perform at least a portion of one or more positioning methods, although the description herein may refer only to the PD 219 being configured to perform, or performing, in accordance with the positioning method(s). The PD 219 may also or alternatively be configured to determine location of the UE 200 using terrestrial-based signals (e.g., at least some of the signals 248) for trilateration, for assistance with obtaining and using the SPS signals 260, or both. The PD 219 may be configured to use one or more other techniques (e.g., relying on the UE's self-reported location (e.g., part of the UE's position beacon)) for determining the location of the UE 200, and may use a combination of techniques (e.g., SPS and terrestrial positioning signals) to determine the location of the UE 200. The PD 219 may include one or more of the sensors 213 (e.g., gyroscope(s), accelerometer(s), magnetometer(s), etc.) that may sense orientation and/or motion of the UE 200 and provide indications thereof that the processor 210 (e.g., the processor 230 and/or the DSP 231) may be configured to use to determine motion (e.g., a velocity vector and/or an acceleration vector) of the UE 200. The PD 219 may be configured to provide indications of uncertainty and/or error in the determined position and/or motion.

Figure 3:
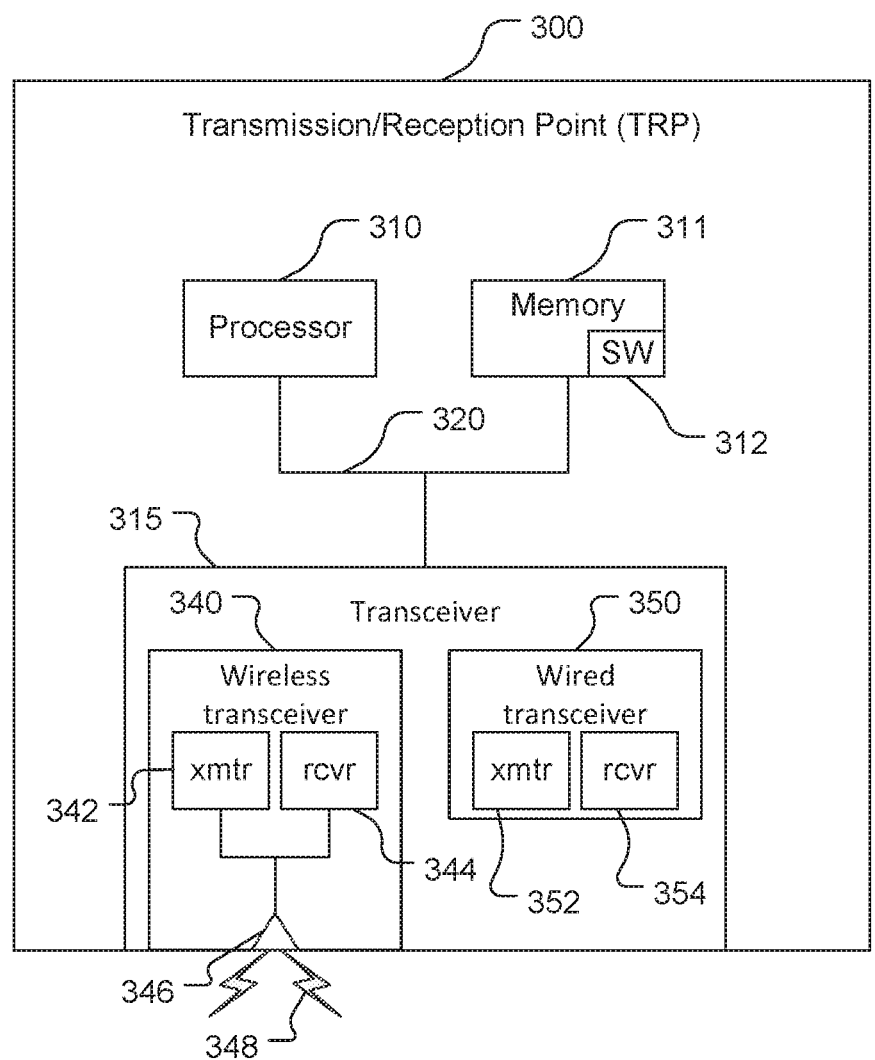
FIG. 3 is a block diagram of components of an example transmission/reception point shown in FIG. 1.
Figure 4:
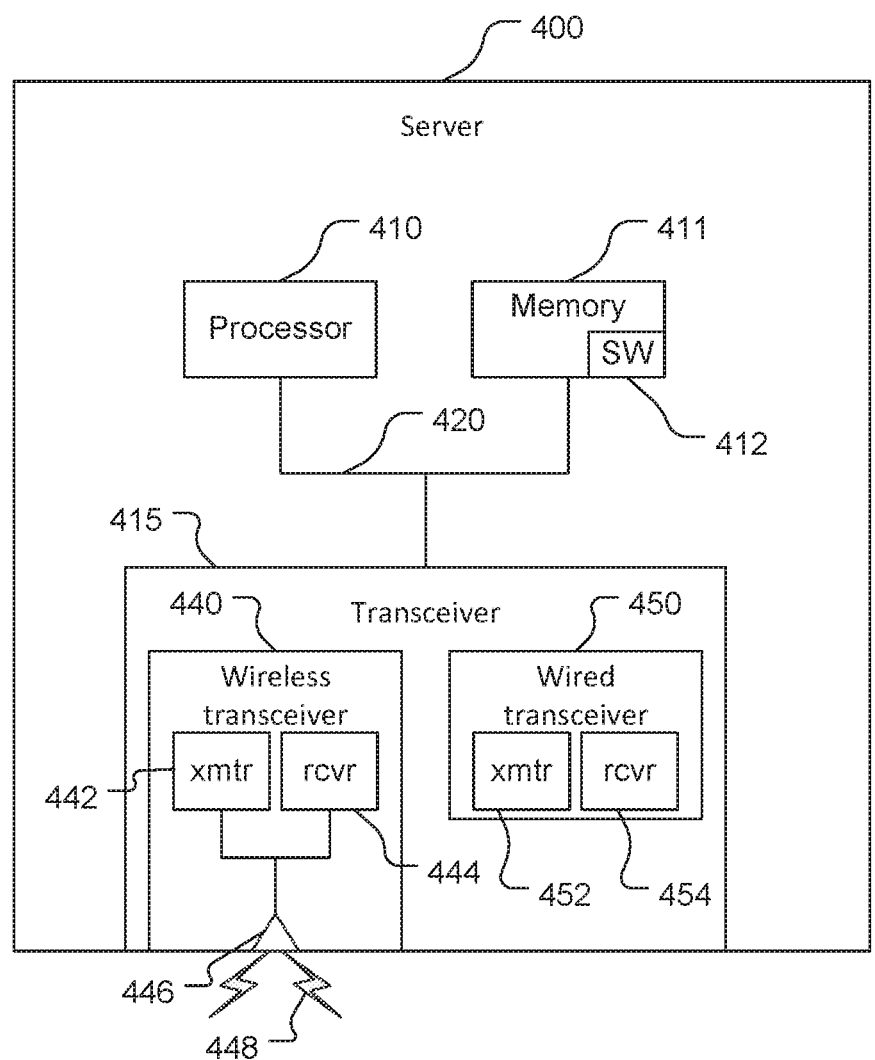
FIG. 4 is a block diagram of components of an example server shown in FIG. 1.

Referring also to FIG. 3, an example of a TRP 300 of the BTSs 120-123 comprises a computing platform including a processor 310, memory 311 including software (SW) 312, and a transceiver 315. The processor 310, the memory 311, and the transceiver 315 may be communicatively coupled to each other by a bus 320 (which may be configured, e.g., for optical and/or electrical communication). One or more of the shown apparatus (e.g., a wireless interface) may be omitted from the TRP 300. The processor 310 may include one or more intelligent hardware devices, e.g., a central processing unit (CPU), a microcontroller, an application specific integrated circuit (ASIC), etc. The processor 310 may comprise multiple processors (e.g., including a general-purpose/application processor, a DSP, a modem processor, a video processor, and/or a sensor processor as shown in FIG. 4). The memory 311 is a non-transitory storage medium that may include random access memory (RAM)), flash memory, disc memory, and/or read-only memory (ROM), etc. The memory 311 stores the software 312 which may be processor-readable, processor-executable software code containing instructions that are configured to, when executed, cause the processor 310 to perform various functions described herein. Alternatively, the software 312 may not be directly executable by the processor 310 but may be configured to cause the processor 310, e.g., when compiled and executed, to perform the functions. The description may refer only to the processor 310 performing a function, but this includes other implementations such as where the processor 310 executes software and/or firmware. The description may refer to the processor 310 performing a function as shorthand for one or more of the processors contained in the processor 310 performing the function. The description may refer to the TRP 300 performing a function as shorthand for one or more appropriate components of the TRP 300 (and thus of one of the BTSs 120-123) performing the function. The processor 310 may include a memory with stored instructions in addition to and/or instead of the memory 311. Functionality of the processor 310 is discussed more fully below.

The transceiver 315 may include a wireless transceiver 340 and a wired transceiver 350 configured to communicate with other devices through wireless connections and wired connections, respectively. For example, the wireless transceiver 340 may include a transmitter 342 and receiver 344 coupled to one or more antennas 346 for transmitting (e.g., on one or more uplink channels) and/or receiving (e.g., on one or more downlink channels) wireless signals 348 and transducing signals from the wireless signals 348 to wired (e.g., electrical and/or optical) signals and from wired (e.g., electrical and/or optical) signals to the wireless signals 348. Thus, the transmitter 342 may include multiple transmitters that may be discrete components or combined/integrated components, and/or the receiver 344 may include multiple receivers that may be discrete components or combined/integrated components. The wireless transceiver 340 may be configured to communicate signals (e.g., with the UE 200, one or more other UEs, and/or one or more other devices) according to a variety of radio access technologies (RATs) such as 5G New Radio (NR), GSM (Global System for Mobiles), UMTS (Universal Mobile Telecommunications System), AMPS (Advanced Mobile Phone System), CDMA (Code Division Multiple Access), WCDMA (Wideband CDMA), LTE (Long-Term Evolution), LTE Direct (LTE-D), 3GPP LTE-V2X (PC5), IEEE 802.11 (including IEEE 802.11p), WiFi, WiFi Direct (WiFi-D), Bluetooth®, Zigbee etc. The wired transceiver 350 may include a transmitter 352 and a receiver 354 configured for wired communication, e.g., with the network 130 to send communications to, and receive communications from, the server 143, for example. The transmitter 352 may include multiple transmitters that may be discrete components or combined/integrated components, and/or the receiver 354 may include multiple receivers that may be discrete components or combined/integrated components. The wired transceiver 350 may be configured, e.g., for optical communication and/or electrical communication.

The configuration of the TRP 300 shown in FIG. 3 is an example and not limiting of the invention, including the claims, and other configurations may be used. For example, the description herein discusses that the TRP 300 is configured to perform or performs several functions, but one or more of these functions may be performed by the server 143 and/or the UE 200 (i.e., the server 143 and/or the UE 200 may be configured to perform one or more of these functions).

Referring also to FIG. 4, a server 400, which is an example of the server 143, comprises a computing platform including a processor 410, memory 411 including software (SW) 412, and a transceiver 415. The processor 410, the memory 411, and the transceiver 415 may be communicatively coupled to each other by a bus 420 (which may be configured, e.g., for optical and/or electrical communication). One or more of the shown apparatus (e.g., a wireless interface) may be omitted from the server 400. The processor 410 may include one or more intelligent hardware devices, e.g., a central processing unit (CPU), a microcontroller, an application specific integrated circuit (ASIC), etc. The processor 410 may comprise multiple processors (e.g., including a general-purpose/application processor, a DSP, a modem processor, a video processor, and/or a sensor processor as shown in FIG. 4). The memory 411 is a non-transitory storage medium that may include random access memory (RAM), flash memory, disc memory, and/or read-only memory (ROM), etc. The memory 411 stores the software 412 which may be processor-readable, processor-executable software code containing instructions that are configured to, when executed, cause the processor 410 to perform various functions described herein. Alternatively, the software 412 may not be directly executable by the processor 410 but may be configured to cause the processor 410, e.g., when compiled and executed, to perform the functions. The description may refer only to the processor 410 performing a function, but this includes other implementations such as where the processor 410 executes software and/or firmware. The description may refer to the processor 410 performing a function as shorthand for one or more of the processors contained in the processor 410 performing the function. The description may refer to the server 400 performing function as shorthand for one or more appropriate components of the server 400 performing the function. The processor 410 may include a memory with stored instructions in addition to and/or instead of the memory 411. Functionality of the processor 410 is discussed more fully below.

The transceiver 415 may include a wireless transceiver 440 and a wired transceiver 450 configured to communicate with other devices through wireless connections and wired connections, respectively. For example, the wireless transceiver 440 may include a transmitter 442 and receiver 444 coupled to one or more antennas 446 for transmitting on one or more uplink channels) and/or receiving (e.g., on one or more downlink channels) wireless signals 448 and transducing signals from the wireless signals 448 to wired (e.g., electrical and/or optical) signals and from wired (e.g., electrical and/or optical) signals to the wireless signals 448. Thus, the transmitter 442 may include multiple transmitters that may be discrete components or combined/integrated components, and/or the receiver 444 may include multiple receivers that may be discrete components or combined/integrated components. The wireless transceiver 440 may be configured to communicate signals (e.g., with the UE 200, one or more other UEs, and/or one or more other devices) according to a variety of radio access technologies (RATS) such as 5G New Radio (NR), GSM (Global System for Mobiles), UMTS (Universal Mobile Telecommunications System), AMPS (Advanced Mobile Phone System), CDMA (Code Division Multiple Access), WCDMA (Wideband. CDMA), LTE (Long-Term Evolution), LTE Direct (LTE-D), 3GPP LTE-V2X (PC5), IEEE 802.11 (including IEEE 802.11p), WiFi, WiFi Direct (WiFi-D), Bluetooth®, Zigbee etc. The wired transceiver 450 may include a transmitter 452 and a receiver 454 configured for wired communication, e.g., with the network 130 to send communications to, and receive communications from, the TRP 300, for example. The transmitter 452 may include multiple transmitters that may be discrete components or combined/integrated components, and/or the receiver 454 may include multiple receivers that may be discrete components or combined/integrated components. The wired transceiver 450 may be configured, e.g., for optical communication and/or electrical communication.

The configuration of the server 400 shown in FIG. 4 is an example and not limiting of the invention, including the claims, and other configurations may be used. For example, the wireless transceiver 440 may be omitted. Also or alternatively, the description herein discusses that the server 400 is configured to perform or performs several functions, but one or more of these functions may be performed by the TRP 300 and/or the UE 200 (i.e., the TRP 300 and/or the UE 200 may be configured to perform one or more of these functions).

Positioning Techniques

One or more of many different positioning techniques (also called positioning methods) may be used to determine position of an entity such as one of the UEs 112-114. For example, known position-determination techniques include RTT, multi-RTT, OTDOA (also called TDOA and including UL-TDOA and DL-TDOA), Enhanced Cell Identification (E-CID), DL-AoD, UL-AoA, etc. RTT uses a time for a signal to travel from one entity to another and back to determine a range between the two entities. The range, plus a known location of a first one of the entities and an angle between the two entities (e.g., an azimuth angle) can be used to determine a location of the second of the entities. In multi-RTT (also called multi-cell RTT), multiple ranges from one entity (e.g., a UE) to other entities (e.g., TRPs) and known locations of the other entities may be used to determine the location of the one entity. In TDOA techniques, the difference in travel times between one entity and other entities may be used to determine relative ranges from the other entities and those, combined with known locations of the other entities may be used to determine the location of the one entity. Angles of arrival and/or departure may be used to help determine location of an entity. For example, an angle of arrival or an angle of departure of a signal combined with a range between devices (determined using signal, e.g., a travel time of the signal, a received power of the signal, etc.) and a known location of one of the devices may be used to determine a location of the other device. The angle of arrival or departure may be an azimuth angle relative to a reference direction such as true north. The angle of arrival or departure may be a zenith angle relative to directly upward from an entity (i.e., relative to radially outward from a center of Earth). E-CID uses the identity of a serving cell, the timing advance (i.e., the difference between receive and transmit times at the UE), estimated timing and power of detected neighbor cell signals, and possibly angle of arrival (e.g., of a signal at the UE from the base station or vice versa) to determine location of the UE. In TDOA, the difference in arrival times at a receiving device of signals from different sources along with known locations of the sources and known offset of transmission times from the sources are used to determine the location of the receiving device.

For positioning techniques using PRS (Positioning Reference Signal) signals (e.g., TDOA and RTT), PRS signals sent by multiple TRPs are measured and the arrival times of the signals, known transmission times, and known locations of the TRPs used to determine ranges from a UE to the TRPs. For example, an RSTD (Reference Signal Time Difference) may be determined for PRS signals received from multiple TRPs and used in a TDOA technique to determine position (location) of the UE. The PRS signals are typically sent using the same power and PRS signals with the same signal characteristics (e.g., same frequency shift) may interfere with each other such that a PRS signal from a more distant TRP may be overwhelmed by a PRS signal from a closer TRP such that the signal from the more distant TRP may not be detected. PRS muting may be used to help reduce interference by muting some PRS signals (reducing the power of the PRS signal, e.g., to zero and thus not transmitting the PRS signal). In this way, a weaker (at the UE) PRS signal may be more easily detected by the UE without a stronger PRS signal interfering with the weaker PRS signal.

Positioning reference signals (PRS) include downlink PRS PRS) and uplink PRS (UL PRS) (which may be called SRS (Sounding Reference Signal) for positioning). PRS may comprise PRS resources or PRS resource sets of a frequency layer. A DL PRS positioning frequency layer (or simply a frequency layer) is a collection of DL PRS resource sets, from one or more TRPs, that have common parameters configured by higher-layer parameters DL-PRS-Positioning-FrequencyLayer, DL-PRS-ResourceSet, and DL-PRS-Resource. Each frequency layer has a DL PRS subcarrier spacing (SCS) for the DL PRS resource sets and the DL PRS resources in the frequency layer. Each frequency layer has a DL PRS cyclic prefix (CP) for the DL PRS resource sets and the DL PRS resources in the frequency layer. Also, a DL PRS Point A parameter defines a frequency of a reference resource block (and the lowest subcarrier of the resource block), with DL PRS resources belonging to the same DL PRS resource set having the same Point A and all DL PRS resource sets belonging to the same frequency layer having the same Point A. A frequency layer also has the same DL PRS bandwidth, the same start PRB (and center frequency), and the same value of comb-size.

A TRP may be configured, e.g., by instructions received from a server and/or by software in the TRP, to send DL PRS per a schedule. According to the schedule, the TRP may send the DL PRS intermittently, e.g., periodically at a consistent interval from an initial transmission. The TRP may be configured to send one or more PRS resource sets. A resource set is a collection of PRS resources across one TRP, with the resources having the same periodicity, a common muting pattern configuration (if any), and the same repetition factor across slots. Each of the PRS resource sets comprises multiple PRS resources, with each PRS resource comprising multiple Resource Elements (REs) that can span multiple Physical Resource Blocks (PRBs) within N (one or more) consecutive symbol(s) within a slot. In an OFDM symbol, a PRS resource occupies consecutive PRBs. Each PRS resource is configured with an RE offset, slot offset, a symbol offset within a slot, and a number of consecutive symbols that the PRS resource may occupy within a slot. The RE offset defines the starting RE offset of the first symbol within a DL PRS resource in frequency. The relative RE offsets of the remaining symbols within a DL PRS resource are defined based on the initial offset. The slot offset is the starting slot of the DL PRS resource with respect to a corresponding resource set slot offset. The symbol offset determines the starting symbol of the DL PRS resource within the starting slot. Transmitted REs may repeat across slots, with each transmission being called a repetition such that there may be multiple repetitions in a PRS resource. The DL PRS resources in a DL PRS resource set are associated with the same TRP and each DL PRS resource has a DL PRS resource ID. A DL PRS resource ID in a DL PRS resource set is associated with a single beam transmitted from a single TRP (although a TRP may transmit one or more beams).

A PRS resource may also be defined by quasi-co-location and start PRB parameters. A quasi-co-location (QCL) parameter may define any quasi-co-location information of the DL PRS resource with other reference signals. The DL PRS may be configured to be QCL type D with a DL PRS or SS/PBCH (Synchronization Signal/Physical Broadcast Channel) Block from a serving cell or a non-serving cell. The DL PRS may be configured to be QCL type C with an SS/PBCH Block from a serving cell or a non-serving cell. The start PRB parameter defines the starting PRB index of the DL PRS resource with respect to reference Point A. The starting PRB index has a granularity of one PRB and may have a minimum value of 0 and a maximum value of 2176 PRBs.

A PRS resource set is a collection of PRS resources with the same periodicity, same muting patter configuration (if any), and the same repetition factor across slots. Every time all repetitions of all PRS resources of the PRS resource set are configured to be transmitted is referred as an "instance". Therefore, an "instance" of a PRS resource set is a specified number of repetitions for each PRS resource and a specified number of PRS resources within the PRS resource set such that once the specified number of repetitions are transmitted for each of the specified number of PRS resources, the instance is complete. An instance may also be referred to as an "occasion." A DL PRS configuration including a DL PRS transmission schedule may be provided to a UE to facilitate (or even enable) the UE to measure the DL PRS.

RTT positioning is an active positioning technique in that RTT uses positioning signals sent by TRPs to UEs and by UEs (that are participating in RTT positioning) to TRPs. The TRPs may send DL-PRS signals that are received by the UEs and the UEs may send SRS (Sounding Reference Signal) signals that are received by multiple TRPs. In 5G multi-RTT, coordinated positioning may be used with the UE sending a single UL-SRS that is received by multiple TRPs instead of sending separate UL-SRS for each TRP. A TRP that participates in multi-RTT will typically search for UEs that are currently camped on that TRP (served UEs, with the TRP being a serving TRP) and also UEs that are camped on neighboring TRPs (neighbor UEs). Neighbor TRPs may be TRPs of a single BTS (e.g., gNB), or may be a TRP of one BTS and a TRP of a separate BTS. For RTT positioning, including multi-RTT positioning, the DL-PRS signal and the UL-SRS signal in a PRS/SRS signal pair used to determine RTT (and thus used to determine range between the UE and the TRP) may occur close in time to each other such that errors due to UE motion and/or UE clock drift and/or TRP clock drift are within acceptable limits. For example, signals in a PRS/SRS signal pair may be transmitted from the TRP and the UE, respectively, within about 10 ms of each other. With SRS signals being sent by UEs, and with PRS and SRS signals being conveyed close in time to each other, it has been found that radio-frequency (RF) signal congestion may result (which may cause excessive noise, etc.) especially if many UEs attempt positioning concurrently and/or that computational congestion may result at the TRPs that are trying to measure many UEs concurrently.

RTT positioning may be UE-based or UE-assisted. In UE-based RTT, the UE 200 determines the RTT and corresponding range to each of the TRPs 300 and the position of the UE 200 based on the ranges to the TRPs 300 and known locations of the TRPs 300. In UE-assisted RTT, the UE 200 measures positioning signals and provides measurement information to the TRP 300, and the TRP 300 determines the RTT and range. The TRP 300 provides ranges to a location server, e.g., the server 400, and the server determines the location of the UE 200, e.g., based on ranges to different TRPs 300. The RTT and/or range may be determined by the TRP 300 that received the signal(s) from the UE 200, by this TRP 300 in combination with one or more other devices, e.g., one or more other TRPs 300 and/or the server 400, or by one or more devices other than the TRP 300 that received the signal(s) from the UE 200.

Various positioning techniques are supported in 5G NR. The NR native positioning methods supported in 5G NR include DL-only positioning methods, UL-only positioning methods, and DL+UL positioning methods. Downlink-based positioning methods include DL-TDOA and DL-AoD. Uplink-based positioning methods include UL-TDOA and UL-AoA. Combined DL+UL-based positioning methods include RTT with one base station and RTT with multiple base stations (multi-RTT).

UE Positioning Signaling Scheduling

The server 400 may be configured to determine that a quantity of UEs seeking positioning service warrants scheduling of UE positioning signals. For example, the server 400 may determine that the quantity of UEs within a geographic region, or served by one or more of the TRPs 300, exceeds a threshold quantity of UEs, e.g., that is associated with undesirable RF congestion and/or undesirable processing congestion by one or more of the TRPs 300. The server 400 may compare the number of UEs presently receiving location service (i.e., positioning service) plus the number of UEs requesting location service against the threshold quantity. The server 400 may be configured to respond to this sum exceeding the threshold quantity by determining and implementing a schedule of UE positioning signal transmissions.

Alternatively, the server 400 may be configured to implement scheduling of UE positioning signal transmissions without determining whether the quantity of UEs requesting and receiving location service exceeds a threshold. The server 400 may be configured to implement scheduling of UE positioning signal transmissions for any UE that requests location service, or proactively implement scheduling of UE positioning signal transmissions by indicating to UEs, even if the UEs have not requested location service, a positioning signal schedule to use if the UE requests location service in the future. The server 400 may be configured to implement (e.g., by providing instructions to the TRP 300 and/or to the UEs 200 via the TRP 300) schedules based on the quantity of UEs, e.g., within the geographic region, or served by the TRP 300, etc. Alternatively, the scheduling may be determined and implemented by the TRP 300 alone, or in conjunction with the server 400.

Figure 5:
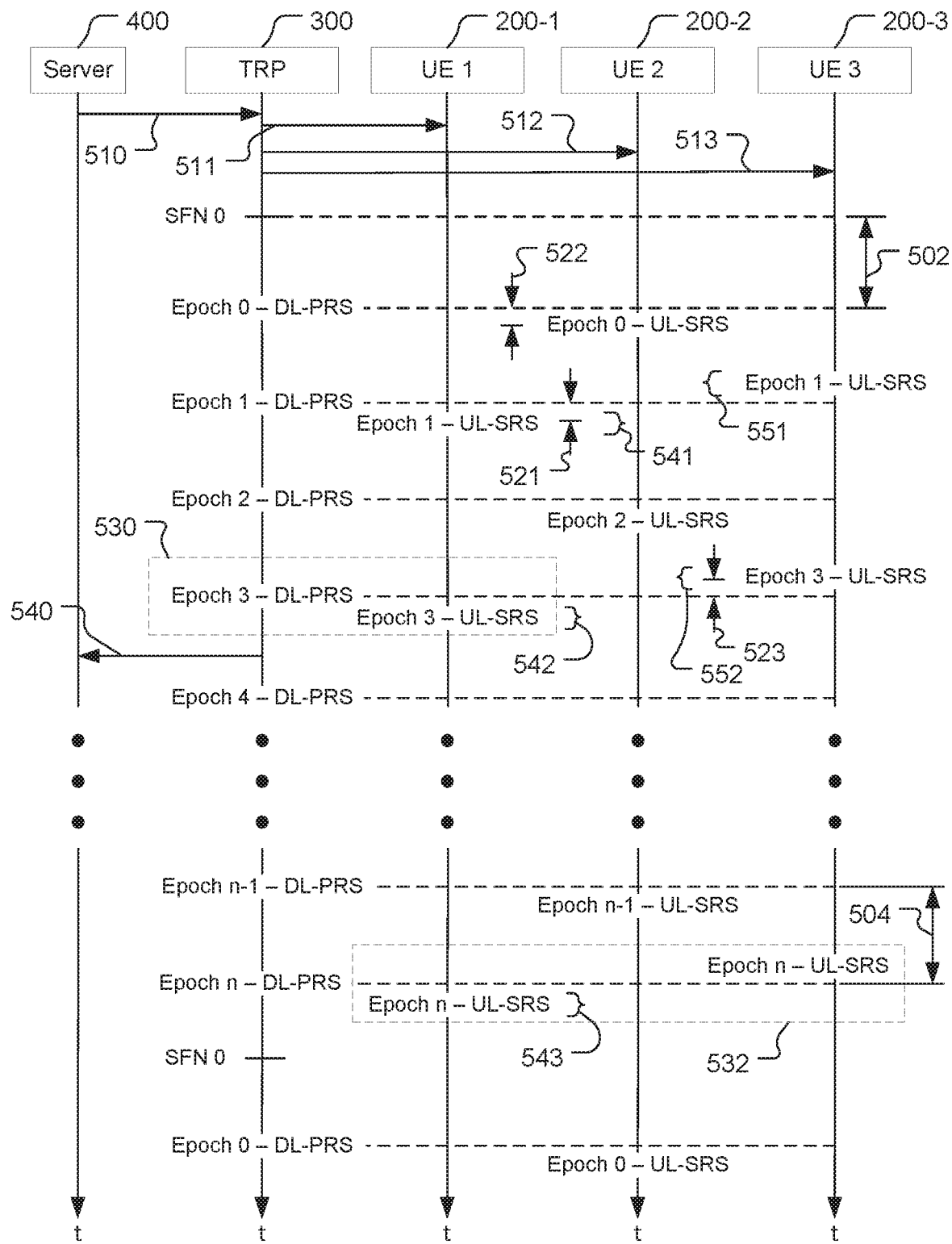
FIG. 5 is a signal flow diagram of signals conveyed between components of a wireless communications system such as that shown in FIG. 1.

Referring also to FIG. 5, the server 400 may be configured to determine scheduling of UE positioning signal transmissions, e.g., to reduce concurrent UE positioning signal transmissions (to reduce RF signaling congestion) and/or to reduce concurrent signal measuring by the TRP 300 (to reduce computational congestion). The server 400 may be configured to determine scheduling information (e.g., allocate uplink signal transmission times) dynamically. The server 400 may be configured to determine and implement a time division multiplexing (TDM) schedule for the UEs 200, with different UEs 200 having different schedules for UE positioning signal transmissions. As shown in FIG. 5, three UEs 200-1, 200-2, 200-3 are served by the TRP 300 and the server 400 implements UE positioning signal transmission scheduling for the UEs 200-1, 220-2, 200-3. The discussion herein describes the server 400 as determining and implementing (e.g., instructing) the scheduling of uplink and downlink positioning signals. One or more of these functions, or portions thereof, may be performed by one or more other devices, e.g., the TRP 300, one or more other TRPs, one or more other servers, etc.

The TRP 300 may be configured, e.g., by instructions received from the server 400 and/or by the software 312, to send downlink positioning reference signals (DL-PRS) per a schedule. According to the schedule, the TRP 300 may send the DL-PRS signals intermittently, e.g., periodically at a consistent interval from an initial transmission. The TRP 300 may be configured to send a DL-PRS signal at known times in a repeating set of sequence frames. The set of sequence frames includes sequence frames that are each divided into one or more subframes that each include one or more slots, with each slot divided into symbols. For example, a frame may be 10 ms and divided into 10 slots of 1 ms each, and each slot divided into 14 symbols of ¹⁄₁₄ ms each. The TRP 300 may be configured to initiate transmission of DL-PRS signals at a beginning of a first sequence frame designated SFN 0 (Sequence Frame Number 0). To help simplify FIG. 5, only SFN 0 at the beginning of each of two consecutive sets of sequence frames are shown (i.e., the other sequence frames are not shown in FIG. 5). The TRP 300 may be configured to send the first DL-PRS signal after a DL-PRS ResourceSetSlotOffset time 502, which is an amount of time typically dictated by the radio network. The TRP 300 sends the DL-PRS signal in an epoch, which is a time window of one or more symbols (possibly multiple slots). The time window of the epoch may be referred to as a time, e.g., a time scheduled to send the DL-PRS signal. The TRP 300 may send further DL-PRS signals at regular intervals after the initial epoch, Epoch 0, e.g., at intervals of a DL-PRS periodicity 504, which may be a different amount of time than the ResourceSetSlotOffset time 502. The DL-PRS periodicity 504 may be greater (i.e., a longer time) than a positioning rate for one or more of the UEs 200-1, 200-2, 200-3, i.e., a period between position determinations or position reports for a UE (e.g., required or requested for the UE). The DL-PRS schedule, e.g., one or more parameters such as periodicity, may be set by the server 400 sending one or more instructions to the TRP 300. The DL-PRS schedule, e.g., periodicity, may be set dynamically by the TRP 300 and/or the server 400, e.g., in response to a quantity of UEs 200 served by the TRP 300 exceeding a threshold, and/or in response to the quantity of UEs 200 served by the TRP 300 requesting or receiving location service exceeding a threshold, and/or one or more other criteria. For example, the DL-PRS periodicity may be reduced (i.e., frequency of DL-PRS transmission increased) in response to the number of UEs 200 increasing (e.g., proportional to the number of UEs, or with different periodicity steps corresponding to different threshold quantities of UEs, etc.). The TRP 300 may be configured, e.g., by the software 312 and/or by instructions from the server 400, to send DL-PRS signals intermittently, but not periodically (i.e., repeatedly but not at evenly-spaced times), or at a combination of some periodically-spaced times and some non-periodically-spaced times.

The server 400 may be configured to determine and provide scheduling information to the UEs. In this example, the server 400 may send scheduling instructions in an instruction communication 510 to the TRP 300 and the TRP 300 may be configured to send at least respective scheduling instructions in instruction communications 511, 512, 513 to the UEs 200-1, 200-2, 200-3. The server 400 may be configured to allocate transmission times to the UEs 200-1, 200-2, 200-3 for transmission of their respective uplink positioning signals, e.g., uplink Sounding Reference Signal (UL-SRS) for positioning. In the discussion herein, the uplink signals are assumed to be UL-SRS for positioning, but other forms of uplink positioning signals may be used. In the example shown in FIG. 5, the server 400 allocates odd epochs to the UEs 200-1, 200-3 and even epochs to the UE 200-2. Thus, the transmission times of the UEs 200-1, 200-3 are interlaced (alternating in time) with the transmission times of the UE 200-2. This allocation is an example only, and other allocations may be used. For example, the three UEs 200-1, 200-2, 200-3 may each have different time allocations (e.g., the UE 200-1 allocated epochs 1, 4, 7, . . ., the UE 200-2 allocated epochs 2, 5, 8, . . . , and the UE 200-3 allocated epochs 3, 6, 9, . . . ). As another example, times (e.g., time windows of epochs) may be allocated in batches of consecutive epochs, e.g., the UE 200-1 allocated epochs 1, 2, 3, 4, the UE 200-2 allocated epochs 5, 6, 7, 8, and the UE 200-3 allocated epochs 9, 10, 11, 12. Still other allocations may be used, and the allocation may depend on various factors such as the number of slots in a frame, the quantity of UEs present (or at least the quantity of UEs served by the TRP 300 and requesting and/or receiving location service), etc.

The server 400 may be configured to determine and allocate transmission times in a variety of ways, for the UEs 200-1, 200-2, 200-3, to implement the transmission schedule. For example, the server 400 may be programmed with a set of different allocations and may assign the allocations to UEs on a rotating basis as new UEs request location service, stepping through each allocation in the set until all allocations have been assigned, and then starting the set over. As another example, the server 400 may assign the allocation used by the last UE to stop receiving location service to the next UE to request location service. Still other techniques for allocating transmission times to the UEs 200-1, 200-2, 200-3 may be used.

The instructions provided to the UEs 200-1, 200-2, 200-3 for uplink positioning signal transmission times may assign one or more symbols to each UE for sending the respective UL-SRS signal. The transmission times for the UL-SRS signals are near, but not necessarily overlapping with, (the one or more symbols of) the epochs of the DL-PRS signal transmissions by the TRP 300. The uplink transmission times may be close enough in time to the epochs of the DL-PRS transmissions to have potential errors due to UE movement and/or clock drift kept within acceptable ranges. An acceptable error source may be one that does not contribute significantly to the end-to-end error. For example, a motion/clock related measurement error source of ⅕ the magnitude of the target accuracy could be considered acceptable as long as the error source is uncorrelated with other error sources. For an end-to-end position target accuracy of 10 m, an acceptable motion/clock error magnitude could therefore be ⅕ of 10 m, i.e., 2 m. A UE may move different distances during a time interval based on the speed of the UE, and a worst-case error impact would be if the UE moves in a straight line. At a speed of 10 m/s, it could be acceptable to space the UL and DL signals apart by 2 m/10 m/s=0.2 seconds because a UE at that speed could move as much as an acceptable magnitude of 2 m in 0.2 seconds. A DL-PRS signal that is close in time to a UL-SRS signal may be identified as an RTT pair that is used to determine RTT between the TRP 300 and the corresponding UE, here the UE 200-1 for an RTT pair 530. Two UL-SRS signals that are both close in time to the same DL-PRS signal may be identified as an uplink-signal pair, e.g., a UL pair 532. The UL-SRS signals in a UL pair, as with the UL pair 532, may have epoch times that are different (e.g., non-identical time windows, even if the time windows overlap). This may be useful to reduce RF congestion and/or useful to help reduce processing congestion by facilitating listening for the UL-SRS signals at different measurement times (over different measurement time windows).

The instructions provided to the UEs 200-1, 200-2, 200-3 for uplink positioning signal transmission times may specify uplink transmission times in a variety of manners. For example, the instructions may specify transmission times, e.g., by specifying a frame, subframe, slot, and symbol combination for each uplink transmission. As another example, the instructions may indicate a frame, subframe, slot, and symbol combination for an initial transmission, and a periodicity of subsequent transmissions. As another example, the instructions may indicate downlink positioning signal epochs (e.g., frame, subframe, slot, and symbol(s) of the DL positioning signal epochs) and an offset for the UL positioning signal transmissions relative to the DL positioning signal epochs (or a subset of the DL positioning signal epochs). Still other techniques for specifying UL transmission times are possible.

The instructions provided by the server 400 to the UEs 200-1, 200-2, 200-3 for uplink positioning signal transmission times may indicate for the UEs 200-1, 200-2, 200-3 to transmit the respective UL-SRS signals at regular intervals of respective UL-SRS periodicities (times from the start of one uplink transmission epoch to the start of the next uplink transmission epoch). The periodicities for each of the UEs 200-1, 200-2, 200-3 may be the same or different depending on the allocation determined by the server 400. Alternatively, the server 400 may be configured to send instructions to cause the UEs 200-1, 200-2, 200-3 to send UL-SRS signals intermittently, but not periodically (i.e., not at evenly-spaced times), or at a combination of some periodically-spaced times and some non-periodically-spaced times.

As shown in FIG. 5, transmission times of uplink signals from the UEs 200-1, 200-2, 200-3 may occur before or after (or may overlap with) transmission times of the downlink signals (e.g., DL-PRS signals) from the TRP 300. In the discussion herein, the downlink signals are assumed to be DL-PRS signals, but other forms of downlink positioning signals may be used. The allocated epochs for the UEs 200-1, 200-2, 200-3 may be offset from the downlink epochs of the TRP 300 by respective DL-to-UL offsets 521, 522, 523. The offsets 521-523 are indications of the amounts of time that the downlink epochs differ from the uplink epochs. Here, the offsets 521-523 are shown as times from the centers of the downlink epochs to the respective uplink epochs, but offsets could be expressed in separate of epochs (e.g., time from the end of a DL epoch to the beginning of an UL epoch or vice versa).

The UEs 200-1, 200-2, 200-3 may be configured to respond to the instructions from the server 400 via the TRP 300 by sending respective UL-SRS signals at instructed times. The UEs 200-1, 200-2, 200-3 and the TRP 300 are reasonably synchronized (in FIG. 5, the UEs 200-1, 200-2, 200-3 and the TRP 300 are shown as being perfectly synchronized, with SFN 0 being at the same time for the TRP 300 and the UEs 200-1, 200-2, 200-3, but there may be some deviation from perfect synchronization). The UEs 200-1, 200-2, 200-3 may use the instructions to schedule the transmission times, e.g., to set a transmission periodicity and/or to schedule specific transmission times.

The UEs 200-1, 200-2, 200-3 may be configured to report information regarding the arrival of the DL-PRS signals and transmission of the UL-SRS signals to facilitate determination of RTT information for use in determining ranges from the UEs 200-1, 200-2, 200-3 to the TRP 300 and thus for determining the positions (locations) of the UEs 200-1, 200-2, 200-3. The UEs 200-1, 200-2, 200-3 may report the arrival and/or transmission information in SRS signals and/or in signals separate from the SRS signals. Regarding downlink signal arrival information, the UEs 200-1, 200-2, 200-3 may send time-of-arrival (ToA) information regarding one or more DL-PRS signals in one or more of the SRS signals to the TRP 300. The ToA information may identify the TRP 300 that sent the DL-PRS signal and the ToA of the DL-PRS signal at the UEs 200-1, 200-2, 200-3. The ToA information may provide an identifier of the DL-PRS message, e.g., a message number. Regarding uplink signal transmission information, the UEs 200-1, 200-2, 200-3 may provide an indication of a time difference labeled UE RxTx (also called $T_{Rx \to Tx}$, or UE $T_{Rx-Tx}$) that is a time difference between the ToA of the DL-PRS signal and the transmission time of the UL-SRS signal proximate in time to the DL-PRS signal. For UL-SRS signals sent after receipt of the DL-PRS signal compared to UL-SRS signals sent before receipt of the DL-PRS signal, the UE RxTx value is opposite in sign. For example, for UL-SRS signals sent after receipt of the DL-PRS signal, the UE RxTx value may be positive, and for UL-SRS signals sent after receipt of the DL-PRS signal, the UE RxTx value may be negative. Using the UE RxTx values, the ToA values of the DL-PRS signal at the UEs 200-1, 200-2, 200-3, the known time of departure (ToD) of the DL-PRS signal from the TRP 300, and the known ToA values of the respective UL-SRS signals at the TRP 300, the TRP 300 can determine the RTTs between the UEs 200-1, 200-2, 200-3 and the TRP 300, from which the TRP 300 can determine the distances between the UEs 200-1, 200-2, 200-3 and the TRP 300 by assuming the speed of light during this propagation time. The TRP 300 may report the RTTs, and/or the ranges corresponding to the RTTs, for the UEs 200-1, 200-2, 200-3 to the server 400, from which the server 400 may determine the locations of the UEs 200-1, 200-2, 200-3.

The TRP 300 may report the RTTs between, and/or ranges to, the UEs 200-1, 200-2, 200-3 individually and/or in batches. For example, the TRP 300 may send a reporting communication 540 to the server 400, with the reporting communication including a batch of determined RTTs and/or a batch of determined ranges. The TRP 300 may send the reporting communications at regular intervals (e.g., according to a reporting periodicity) and/or in an ad hoc fashion, e.g., in response to a trigger such as a threshold quantity of RTTs being determined and/or a threshold quantity of ranges being determined. The TRP 300 may change the reporting periodicity dynamically in response to a change in a number of UEs present and/or in response to a change in a rate at which RTTs and/or ranges are being determined.

The server 400 (and/or the TRP 300) may be configured to control timing of signal measurements by the TRP 300 for different UEs 200-1, 200-2, 200-3. For example, the server 400 may be configured to send instructions to the TRP 300 to search for a signal with a code corresponding to the UE 200-1 only during measurement time windows 541, 542, 543 that include the epochs during which the UE 200-1 is scheduled to transmit the UL-SRS signals, and to search for a signal with a code corresponding to the UE 200-3 only during measurement time windows 551, 552 that include the epochs during which the UE 200-3 is scheduled to transmit the UL-SRS signals. As another example, the TRP 300 may be configured to search for the signal with a code corresponding to the UE 200-1 only during the measurement time windows 541, 542, 543 in response to the TRP 300 analyzing the instructions from the server 400 to the UE 200-1 to schedule sending of the UL-SRS from the UE 200-1. The TRP 300 may thus be configured to measure for specific UE uplink signals during respective measurement time windows, and the measurement time windows may be before or after the transmission of DL-PRS signals sent in close time proximity to the UL-SRS signals. The measurement times at the TRP 300 may be offset from the transmission times from the UEs 200-1, 200-2, 200-3 to account for travel time of UL-SRS signals between the UEs 200-1, 200-2, 200-3 and the TRP 300.

The TRP 300 may process UL-SRS signals in accordance with which UL-SRS signals the TRP 300 was measuring (listening for) at the respective measurement time windows. The use of measurement time windows at different times (e.g., spanning different (non-identical) time windows even if the windows overlap) for different UEs may help spread the measurement times out and thus help spread the processing times out, reducing processing congestion at the TRP 300.

Operation

Figure 6:
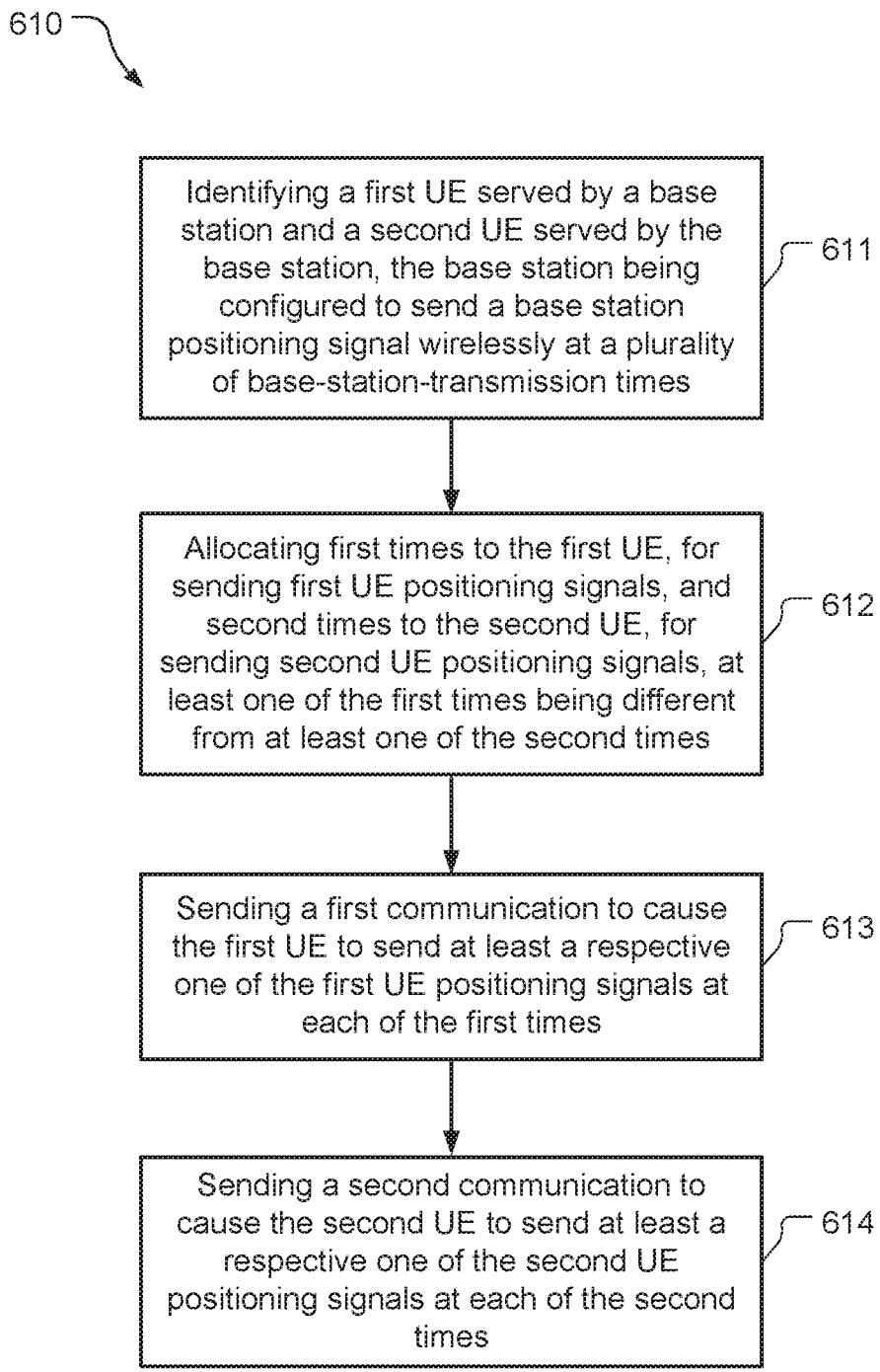
FIG. 6 is a block flow diagram of a method of coordinating positioning signaling.

Referring to FIG. 6, with further reference to FIGS. 1-5, a method 610 of coordinating positioning signaling includes the stages shown. The method 610 is, however, an example only and not limiting. The method 610 may be altered, e.g., by having stages added, removed, rearranged, combined, performed concurrently, and/or having single stages split into multiple stages. For example, one or more stages may occur before, and/or one or more stages may occur after, the stages shown in FIG. 6. For example, one or more measurements may be taken and values thereof provided for use in determining a location of a UE. As another example, measurement values may be provided to a location server for collecting measurement information for multiple UEs and determining the locations of the UEs.

At stage 611, the method 610 includes identifying a first UE served by a base station and a second UE served by the base station, the base station being configured to send a base station positioning signal wirelessly at a plurality of base-station-transmission times. For example, the server 400 may communicate, via the transceiver 415 (e.g., the wired transceiver 450) with the TRP 300 to receive a list of UEs that the TRP 300 is serving. Thus, the processor 410 and the wired transceiver 450, and possibly the software 412, may comprise means for identifying the first and second UEs. As another example, the processor 310 may access the memory 311 to obtain a list of UEs presently served by the TRP 300. Thus, the processor 310 and the memory 311, and possibly the software 312, may comprise means for identifying the first and second UEs. The TRP 300 may be configured to send positioning signals at the plurality of base-station-transmission times according to instructions of the software 312 in the memory 311. The base-station-transmission times may be time windows corresponding to epochs, e.g., Epoch 0—DL-PRS, Epoch 1—DL-PRS, etc. shown in FIG. 5 during which the TRP 300 may send DL-PRS signals.

At stage 612, the method 610 includes allocating first times to the first UE, for sending first UE positioning signals, and second times to the second UE, for sending second UE positioning signals, at least one of the first times being different from at least one of the second times. The first times and/or second times may be time windows corresponding to epochs during which UEs send UL-SRS signals. For example, the server 400 may determine to allocate different times for uplink positioning signal transmissions to different UEs, e.g., the UE 200-1 and the UE 200-2. The server 400 may determine to allocate times in response to a trigger condition such as a quantity of UEs exceeding a threshold. The threshold quantity may be for the number of UEs, e.g., served by the TRP 300, or served by the TRP and receiving location service, or served by the TRP 300 and either receiving location service or having requested location service, etc. One or more other trigger conditions may be used. The server 400 may allocate the first and second times in a variety of manners, e.g., as discussed above. The processor 410, possibly in combination with the software 412 of the memory 411, may comprise means for allocating the first times and the second times. Alternatively, the TRP 300 alone, or in combination with the server 400 and/or one or more other devices (e.g., one or more other TRPs and/or one or more other servers) may allocate the first times and the second times. Thus, for example, the processor 310, possibly in combination with the software 312 of the memory 311, may comprise means for allocating the first times and the second times.

At stage 613, the method 610 includes sending a first communication to cause the first UE to send at least a respective one of the first UE positioning signals at each of the first times. For example, the server 400, e.g., the processor 410, may send the communication 510 via the transceiver 415, e.g., via the wired transmitter 452, to the TRP 300 to cause the TRP 300 send the communication 511 to the UE 200-1 with indications of the first times. The communication 511 may cause the UE 200-1 to send a UL positioning signal at each of the first times, and only at the first times. Thus, the processor 410, possibly in combination with the memory 411 (e.g., the software 412), and the wired transmitter 452 may comprise means for sending the first communication. The UE 200-1 may respond to receiving the instructions by scheduling to send an UL-SRS signal at one or more of the indicated times, and only at the one or more indicated times.

At stage 614, the method 610 includes sending a second communication to cause the second UE to send at least a respective one of the second UE positioning signals at each of the second times. For example, the server 400, e.g., the processor 410, may send the communication 510 via the transceiver 415, e.g., via the wired transmitter 452, to the TRP 300 to cause the TRP 300 send the communication 512 to the UE 200-2 with indications of the second times. The communication 512 may cause the UE 200-2 to send a UL positioning signal at each of the second times, and only at the second times. Thus, the processor 410, possibly in combination with the memory 411 (e.g., the software 412), and the wired transmitter 452 may comprise means for sending the second communication. The UE 200-2 may respond to receiving the instructions by scheduling to send an UL-SRS signal at one or more of the indicated times, and only at the one or more indicated times.

The method 610 may include one or more of the following features. For example, the first times may occur less often than the base-station-transmission times. The server 400 (or the TRP 300) (the means for allocating) may allocate the first times such that the first times are less frequent (there are fewer first times per unit time than there are base-station-transmission times). As another example, the first times and the second times are allocated to be proximate in time to respective ones of the base-station-transmission times. The server 400 (or the TRP 300) (the means for allocating) may allocate the first times so that the first UE positioning are sent proximate in time to the base station positioning signals being sent. For example, the first times and the base-station-transmission times may be close enough to ensure that errors in determining RTT range due to UE motion and clock drift are within acceptable limits. For example, the first times and the base-station-transmission times may be scheduled such that a beginning of the first UE positioning signal and a beginning of a corresponding base station positioning signal (e.g., the base station positioning signal whose base-station-transmission time is closest to the transmission time of the respective first UE positioning signal) are separated by no more than 10 ms. As another example feature of the method 610, the base station may be controlled to listen for the first UE positioning signals only during first-signal-measurement times. The first-signal-measurement times may include the first times offset for travel time between the first UE and the base station. For example, the server 400 may instruct the TRP 300 (or the processor 310 may execute instructions of the software 312) to listen for a the UE positioning signal from the UE 200-1 only during times that the UE 200-1 has been scheduled to send a respective positioning signal, e.g., a respective UL-SRS signal, offset (later in time) by the travel time from the UE 200-1 to the TRP 300. Thus, the wired transmitter 452 and the processor 410, possibly in combination with the software 412, may comprise means for controlling the base station to listen for the first UE positioning signals only during first-signal-measurement times. The processor 310, possibly in combination with the software 312, may comprise means for controlling the base station to listen for the first UE positioning signals only during first-signal-measurement times. The first-signal-measurement times may be time windows corresponding to epoch time windows in which the UE is scheduled to send the UL-SRS signal.

Also or alternatively, the method 610 may include one or more of the following features. For example, each respective one of the first times is before a respective one of the base-station-transmission times to which the respective one of the first times is closest in time. As another example, the first times and second times may comprise pairs of times, with each of the pairs of times comprising: a respective one of the first times that is closest in time, of the first times, to a respective one of the base-station-transmission times; and a respective one of the second times that is closest in time, of the second times, to the respective one of the base-station-transmission times, where the respective one of the first times is different than the respective one of the second times. Thus, for example, the UE 200-1 and the UE 200-3 are instructed to send respective UL-SRS signals proximate to the same DL-PRS signals, but at different (non-identical) epoch time windows, which may help reduce RF congestion and/or signal processing congestion. As another example feature of the method 610, a third communication may be sent to change the first times to third times, at least one of the third times being different from the first times. For example, the server 400 may dynamically determine and allocate UL positioning signal transmission times and send instructions to implement these times, including to instruct UEs that have been previously instructed to transmit at certain times to change the times at which the UE will transmit the UL positioning signals. For example, the server 400 may instruct the UE 200-1 to change from transmitting UL-SRS signals at odd epochs to even epochs, or from the odd epochs to the first four epochs of a set of sequence frames, or according to another schedule. The processor 410, possibly in combination with the software 412, and the wired transmitter 452 may comprise means for sending the third communication. The processor 310, possibly in combination with the software 312, may comprise means for sending the third communication.

Also or alternatively, the method 610 may include one or more of the following features. For example, the method 610 may include causing the base station to change the plurality of base-station-transmission times in response to a trigger condition. For example, the processor 410 (possibly in combination with the software 412) may, via the wired transmitter 452, instruct the TRP 300 to change when the TRP 300 will send the DL-PRS signals, e.g., by increasing or decreasing a frequency of (decreasing or increasing a periodicity of) the DL-PRS signal transmissions. Thus, the processor 410 (and possibly the software 412) and the transmitter 452 may comprise means for causing the base station to change the base-station-transmission times. The processor 310, possibly in combination with the software 312, may cause the TRP 300 to change when the TRP 300 will send the DL-PRS signals. Thus, the processor 310 (and possibly the software 312) may comprise means for causing the base station to change the base-station-transmission times. The trigger condition may be a threshold quantity of UEs being exceeded. The threshold quantity may be, for example, of UEs served by the TRP 300, of UEs served by the TRP 300 and receiving location service, of UEs served by the TRP 300 and receiving or having requested location service, etc. As another example, the threshold quantity may be a threshold quantity of UEs per epoch. The threshold quantity may be an absolute number, e.g., 50, or a relative number, e.g., 50 more UEs than in another epoch. For example, if there are more than a threshold number of UEs allocated to a particular epoch (e.g., more than an absolute quantity or more than a threshold number more than another epoch), then the server 400 may assign some of those UEs to a different epoch, e.g., such that the (relative) quantity is below the threshold quantity. For example, if there are 30 UEs assigned to one epoch and 10 UEs assigned to another epoch, the server 400 may send instructions to re-allocate the UL positioning signal transmission times so that there are 20 UEs assigned to each of these epochs.

Also or alternatively, the method 610 may include one or more of the following features. For example, all of the first times may be different from all of the second times. Thus, the first times may span time windows that are non-identical to the time windows spanned by the second times. As another example, the first times may alternate in time with the second times.

Figure 7:
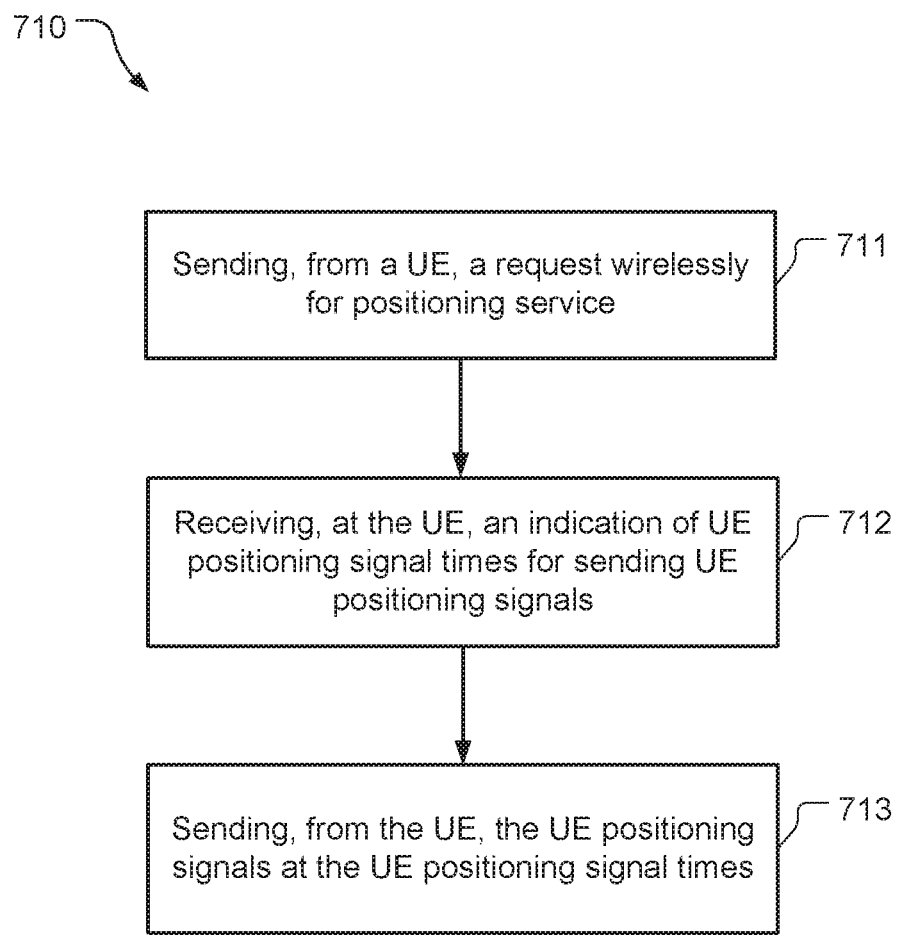
FIG. 7 is another block flow diagram of a method of coordinating positioning signaling.

Referring to FIG. 7, with further reference to FIGS. 1-5, a method 710 of coordinating positioning signaling includes the stages shown. The method 710 is, however, an example only and not limiting. The method 710 may be altered, e.g., by having stages added, removed, rearranged, combined, performed concurrently, and/or having single stages split into multiple stages. For example, one or more stages may occur before, and/or one or more stages may occur after, the stages shown in FIG. 7.

At stage 711, the method 710 includes sending, from a user equipment (UE), a request wirelessly for positioning service. For example, the processor 210 (e.g., the processor 230), possibly in conjunction with the software 212 of the memory 211, may produce and send a request for positioning service wirelessly via the wireless transmitter 242 to the TRP 300. The processor 210), possibly in conjunction with the software 212 of the memory 211, and the transmitter 242 may comprise means for sending the request. The request may be a request for the server 400 to provide location service (e.g., determine and provide the location of the UE 200 to the UE 200 and/or to another device).

At stage 712, the method 710 includes receiving, at the UE, an indication of UE positioning signal times for sending UE positioning signals. For example, the processor 210 of the UE 200-1 may receive the communication 511 from the TRP 300, via the wireless receiver 244, indicating a schedule of times for the UE 200-1 to send UL positioning signals, e.g., UL-SRS signals. The processor 210 and the wireless receiver 244 may comprise means for receiving the indication of UE positioning signal times. The indication may be, for example, a schedule of positioning signal times in a set of sequence frames (e.g., combinations of frame, subframe, slot, symbol of the times themselves (relative to a reference time, e.g., a beginning of sequence frame number 0)), or times from which the transmission times may be derived (e.g., base-station-transmission times (and possibly offsets relative to those times), an indication of a subset of the base-station-transmission times, etc.).

At stage 713, the method 710 includes sending, from the UE, the UE positioning signals at the UE positioning signal times. For example, the processor 210 (e.g., the processor 230) may cause UE positioning signals (e.g., UL-SRS signals) to be sent via the wireless transmitter 242, e.g., to the TRP 300 only during the UE positioning signal times, e.g., only during epochs for the UL-SRS signals. The processor 210 and the wireless transmitter 242 may comprise means for receiving the indication of UE positioning signal times.

Other Considerations

Other examples and implementations are within the scope and spirit of the disclosure and appended claims. For example, due to the nature of software and computers, functions described above can be implemented using software executed by a processor, hardware, firmware, hardwiring, or a combination of any of these. Features implementing functions may also be physically located at various positions, including being distributed such that portions of functions are implemented at different physical locations. For example, one or more functions, or one or more portions thereof, discussed above as occurring in the server 400 (e.g., for determining and allocating uplink transmission times) may be performed outside of the server 400 such as by the TRP 300.

As used herein, the singular forms "a," "an," and "the" include the plural forms as well, unless the context clearly indicates otherwise. The terms "comprises," "comprising," "includes," and/or "including," as used herein, specify the presence of stated features, integers, steps, operations, elements, and/or components, but do not preclude the presence or addition of one or more other features, integers, steps, operations, elements, components, and/or groups thereof.

Also, as used herein, "or" as used in a list of items prefaced by "at least one of" or prefaced by "one or more of" indicates a disjunctive list such that, for example, a list of "at least one of A, B, or C," or a list of "one or more of A, B, or C" means A or B or C or AB or AC or BC or ABC (i.e., A and B and C), or combinations with more than one feature (e.g., AA, AAB, ABBC, etc.).

Substantial variations may be made in accordance with specific requirements. For example, customized hardware might also be used, and/or particular elements might be implemented in hardware, software (including portable software, such as applets, etc.) executed by a processor, or both. Further, connection to other computing devices such as network input/output devices may be employed.

As used herein, unless otherwise stated, a statement that a function or operation is "based on" an item or condition means that the function or operation is based on the stated item or condition and may be based on one or more items and/or conditions in addition to the stated item or condition.

The systems and devices discussed above are examples. Various configurations may omit, substitute, or add various procedures or components as appropriate. For instance, features described with respect to certain configurations may be combined in various other configurations. Different aspects and elements of the configurations may be combined in a similar manner. Also, technology evolves and, thus, many of the elements are examples and do not limit the scope of the disclosure or claims.

A wireless communication system is one in which communications are conveyed wirelessly, i.e., by electromagnetic and/or acoustic waves propagating through atmospheric space rather than through a wire or other physical connection. A wireless communication network may not have all communications transmitted wirelessly, but is configured to have at least some communications transmitted wirelessly. Further, the term "wireless communication device," or similar term, does not require that the functionality of the device is exclusively, or evenly primarily, for communication, or that the device be a mobile device, but indicates that the device includes wireless communication capability (one-way or two-way), e.g., includes at least one radio (each radio being part of a transmitter, receiver, or transceiver) for wireless communication.

Specific details are given in the description to provide a thorough understanding of example configurations (including implementations)). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations provides a description for implementing described techniques. Various changes may be made in the function and arrangement of elements without departing from the spirit or scope of the disclosure.

The terms "processor-readable medium," "machine-readable medium," and "computer-readable medium," as used herein, refer to any medium that participates in providing data that causes a machine to operate in a specific fashion. Using a computing platform, various processor-readable media might be involved in providing instructions/code to processor(s) for execution and/or might be used to store and/or carry such instructions/code as signals). In many implementations, a processor-readable medium is a physical and/or tangible storage medium. Such a medium may take many forms, including but not limited to, non-volatile media and volatile media. Non-volatile media include, for example, optical and/or magnetic disks. Volatile media include, without limitation, dynamic memory.

Having described several example configurations, various modifications, alternative constructions, and equivalents may be used without departing from the spirit of the disclosure. For example, the above elements may be components of a larger system, wherein other rules may take precedence over or otherwise modify the application of the invention. Also, a number of operations may be undertaken before, during, or after the above elements are considered. Accordingly, the above description does not bound the scope of the claims.

A statement that a value exceeds (or is more than or above) a first threshold value is equivalent to a statement that the value meets or exceeds a second threshold value that is slightly greater than the first threshold value, e.g., the second threshold value being one value higher than the first threshold value in the resolution of a computing system. A statement that a value is less than (or is within or below) a first threshold value is equivalent to a statement that the value is less than or equal to a second threshold value that is slightly lower than the first threshold value, e.g., the second threshold value being one value lower than the first threshold value in the resolution of a computing system.

The invention claimed is:

1. A method of coordinating positioning signaling, the method comprising:
    identifying a first user equipment (UE) served by a base station and a second UE served by the base station, the base station being configured to send a base station positioning signal wirelessly at a plurality of base-station-transmission times;
    allocating first times to the first UE, for sending first UE positioning signals, and second times to the second UE, for sending second UE positioning signals, at least one of the first times being different from at least one of the second times;
    sending a first communication to cause the first UE to send at least a respective one of the first UE positioning signals at each of the first times; and
    sending a second communication to cause the second UE to send at least a respective one of the second UE positioning signals at each of the second times.

2. The method of claim 1, wherein the first times occur less often than the plurality of base-station-transmission times.

3. The method of claim 1, wherein the first times and the second times are allocated to be proximate in time to respective ones of the plurality of base-station-transmission times.

4. The method of claim 1, further comprising controlling the base station to listen for the first UE positioning signals only during first-signal-measurement times.

5. The method of claim 4, wherein the first-signal-measurement times include the first times offset for travel time between the first UE and the base station.

6. The method of claim 1, wherein each respective one of the first times is before a respective one of the plurality of base-station-transmission times to which the respective one of the first times is closest in time.

7. The method of claim 1, wherein:
    the first times and the second times comprise a plurality of pairs of times;
    each of the plurality of pairs of times comprises:
        a respective one of the first times that is closest in time, of the first times, to a respective one of the plurality of base-station-transmission times; and
        a respective one of the second times that is closest in time, of the second times, to the respective one of the plurality of base-station-transmission times; and
    the respective one of the first times is different than the respective one of the second times.

8. The method of claim 1, further comprising sending a third communication to change the first times to third times, at least one of the third times being different from the first times.

9. The method of claim 1, further comprising causing the base station to change the plurality of base-station-transmission times in response to a trigger condition.

10. The method of claim 9, wherein the trigger condition is a threshold quantity of UEs being exceeded.

11. The method of claim 10, wherein the threshold quantity of UEs is a threshold quantity of UEs per epoch.

12. The method of claim 1, wherein all of the first times are different from all of the second times.

13. The method of claim 1, wherein the first times alternate in time with the second times.

14. The method of claim 1, wherein the first times and the second times are respective time portions of a set of sequence frames, and wherein the set of sequence frames repeats.

15. A system for coordinating positioning signaling, the system comprising:
    a transceiver; and
    a processor communicatively coupled to the transceiver and configured to:
        identify a first user equipment (UE) served by a base station and a second UE served by the base station, the base station being configured to send a base station positioning signal wirelessly at a plurality of base-station-transmission times;
        allocate first times to the first UE, for sending first UE positioning signals, and second times to the second UE, for sending second UE positioning signals, at least one of the first times being different from at least one of the second times;
        send a first communication, via the transceiver, to cause the first UE to send at least a respective one of the first UE positioning signals at each of the first times; and send a second communication, via the transceiver, to cause the second UE to send at least a respective one of the second UE positioning signals at each of the second times.

16. The system of claim 15, wherein the processor is configured to allocate the first times such that the first times are less frequent than the plurality of base-station-transmission times.

17. The system of claim 15, wherein the processor is configured to allocate the first times and the second times to be proximate in time to respective ones of the plurality of base-station-transmission times.

18. The system of claim 15, wherein the processor is further configured to control the base station to listen for the first UE positioning signals only during first-signal-measurement times.

19. The system of claim 18, wherein the first-signal-measurement times include the first times offset for travel time between the first UE and the base station.

20. The system of claim 15, wherein the processor is configured to allocate the first times and the second times such that:
the first times and the second times comprise a plurality of pairs of times;
each of the plurality of pairs of times comprises:
a respective one of the first times that is closest in time, of the first times, to a respective one of the plurality of base-station-transmission times; and
a respective one of the second times that is closest in time, of the second times, to the respective one of the plurality of base-station-transmission times; and
the respective one of the first times is different than the respective one of the second times.

21. The system of claim 15, wherein the processor is configured to send a third communication to change the first times to third times, at least one of the third times being different from the first times.

22. The system of claim 15, wherein the processor is configured to cause the base station to change the plurality of base-station-transmission times in response to a trigger condition.

23. The system of claim 22, wherein the trigger condition is a threshold quantity of UEs being exceeded.

24. The system of claim 23, wherein the threshold quantity of UEs is a threshold quantity of UEs per epoch.

25. A system for coordinating positioning signaling, the system comprising:
means for identifying a first user equipment (UE) served by a base station and a second UE served by the base station, the base station being configured to send a base station positioning signal wirelessly at a plurality of base-station-transmission times;
means for allocating first times to the first UE, for sending first UE positioning signals, and second times to the second UE, for sending second UE positioning signals, at least one of the first times being different from at least one of the second times;
means for sending a first communication to cause the first UE to send at least a respective one of the first UE positioning signals at each of the first times; and
means for sending a second communication to cause the second UE to send at least a respective one of the second UE positioning signals at each of the second times.

26. The system of claim 25, wherein the means for allocating are for allocating the first times such that the first times occur less often than the plurality of base-station-transmission times.

27. The system of claim 25, wherein the means for allocating are for allocating the first times and the second times to be proximate in time to respective ones of the plurality of base-station-transmission times.

28. The system of claim 25, further comprising means for controlling the base station to listen for the first UE positioning signals only during first-signal-measurement times.

29. The system of claim 28, wherein the first-signal-measurement times include the first times offset for travel time between the first UE and the base station.

30. The system of claim 25, wherein the means for allocating are for allocating the first times and the second times such that:
the first times and the second times comprise a plurality of pairs of times;
each of the plurality of pairs of times comprises:
a respective one of the first times that is closest in time, of the first times, to a respective one of the plurality of base-station-transmission times; and
a respective one of the second times that is closest in time, of the second times, to the respective one of the plurality of base-station-transmission times; and
the respective one of the first times is different than the respective one of the second times.

31. The system of claim 25, further comprising means for sending a third communication to change the first times to third times, at least one of the third times being different from the first times.

32. The system of claim 25, further comprising means for causing the base station to change the plurality of base-station-transmission times in response to a trigger condition.

33. The system of claim 32, wherein the trigger condition is a threshold quantity of UEs being exceeded.

34. The system of claim 33, wherein the threshold quantity of UEs is a threshold quantity of UEs per epoch.

35. A non-transitory, processor-readable storage medium comprising processor-readable instructions configured to cause a processor to:
identify a first user equipment (UE) served by a base station and a second UE served by the base station, the base station being configured to send a base station positioning signal wirelessly at a plurality of base-station-transmission times;
allocate first times to the first UE, for sending first UE positioning signals, and second times to the second UE, for sending second UE positioning signals, at least one of the first times being different from at least one of the second times;
send a first communication to cause the first UE to send at least a respective one of the first UE positioning signals at each of the first times; and
send a second communication to cause the second UE to send at least a respective one of the second UE positioning signals at each of the second times.

36. The storage medium of claim 35, wherein the instructions configured to allocate the first times are configured to allocate the first times such that the first times occur less often than the plurality of base-station-transmission times.

37. The storage medium of claim 35, wherein the instructions configured to allocate the first times and the second times are configured to allocate the first times and the second times to be proximate in time to respective ones of the plurality of base-station-transmission times.

38. The storage medium of claim 35, further comprising instructions configured to cause the base station to listen for the first UE positioning signals only during first-signal-measurement times.

39. The storage medium of claim 38, wherein the first-signal-measurement times include the first times offset for travel time between the first UE and the base station.

40. The storage medium of claim 35, wherein:
the first times and the second times comprise a plurality of pairs of times;
each of the plurality of pairs of times comprises:
a respective one of the first times that is closest in time, of the first times, to a respective one of the plurality of base-station-transmission times; and
a respective one of the second times that is closest in time, of the second times, to the respective one of the plurality of base-station-transmission times; and
the respective one of the first times is different than the respective one of the second times.

41. The storage medium of claim 35, further comprising instructions configured to cause the processor to send a third communication to change the first times to third times, at least one of the third times being different from the first times.

42. The storage medium of claim 35, further comprising instructions configured to cause the processor to cause the base station to change the plurality of base-station-transmission times in response to a trigger condition.

43. The storage medium of claim 42, wherein the trigger condition is a threshold quantity of UEs being exceeded.

44. The storage medium of claim 43, wherein the threshold quantity of UEs is a threshold quantity of UEs per epoch.

* * * * *